(12) United States Patent  (10) Patent No.: US 8,216,161 B2
Darlington et al.  (45) Date of Patent: *Jul. 10, 2012

(54) OPTIMIZATION AND FEEDBACK CONTROL OF HIFU POWER DEPOSITION THROUGH THE FREQUENCY ANALYSIS OF BACKSCATTERED HIFU SIGNALS

(75) Inventors: Gregory P. Darlington, Snohomish, WA (US); Charles D. Emery, Issaquah, WA (US); Justin A. Reed, Seattle, WA (US)

(73) Assignee: Mirabilis Medica Inc., Bothell, WA (US)

( * ) Notice: Subject to any disclaimer, the term of this patent is extended or adjusted under 35 U.S.C. 154(b) by 868 days.

This patent is subject to a terminal disclaimer.

(21) Appl. No.: 12/187,318

(22) Filed: Aug. 6, 2008

(65) Prior Publication Data

US 2010/0036291 A1  Feb. 11, 2010

(51) Int. Cl.
*A61H 1/00* (2006.01)
(52) U.S. Cl. .......................................................... 601/2
(58) Field of Classification Search .................. 601/2
See application file for complete search history.

(56) References Cited

U.S. PATENT DOCUMENTS

| 3,470,868 | A | 10/1969 | Krause |
| 3,480,002 | A | 11/1969 | Flaherty |
| 3,676,584 | A | 7/1972 | Plakas |
| 3,941,112 | A | 3/1976 | Habert |
| 4,059,098 | A | 11/1977 | Murdock |
| 4,097,835 | A | 6/1978 | Green |
| 4,185,502 | A | 1/1980 | Frank |
| 4,282,755 | A | 8/1981 | Gardineer |
| 4,347,850 | A | 9/1982 | Kelly-Fry |
| 4,484,569 | A | 11/1984 | Driller |
| 4,742,829 | A | 5/1988 | Law |

(Continued)

FOREIGN PATENT DOCUMENTS

EP  0301360 B1  2/1989

(Continued)

OTHER PUBLICATIONS

International Search Report and Written Opinion mailed May 18, 2010, in corresponding International Application No. PCT/US2009/053050, filed Aug. 6, 2009, 15 pages.

(Continued)

*Primary Examiner* — Tse Chen
*Assistant Examiner* — Hien Nguyen
(74) *Attorney, Agent, or Firm* — Christensen O'connor Johnson Kindness PLLC

(57) ABSTRACT

A system and method for dynamically adjusting the energy of HIFU signals delivered to a patient, and/or to aid in visualizing the likely degree and location of HIFU effects on patient tissue. The system transmits a HIFU signal into a patient and receives echoes therefrom. The echo signals are analyzed to determine the energy of the signals in a first range, such as at one or more harmonics and/or sub-harmonics of the fundamental frequency of the HIFU signal, and energy of the echo signals in a second range such as at the fundamental frequency of the HIFU signal. Based on the comparison, the energy and/or focus of the HIFU signals delivered to the patient is adjusted. An image of the compared echo signal powers in two or more frequency ranges may also be displayed for a user or used to adjust the focus point of the HIFU signals.

20 Claims, 19 Drawing Sheets

U.S. PATENT DOCUMENTS

| | | | |
|---|---|---|---|
| 4,756,313 | A | 7/1988 | Terwilliger |
| 4,819,621 | A | 4/1989 | Ueberle |
| 4,835,689 | A | 5/1989 | O'Donnell |
| 4,858,613 | A | 8/1989 | Fry |
| 4,865,042 | A | 9/1989 | Umemura |
| 4,893,624 | A | 1/1990 | Lele |
| 5,005,579 | A | 4/1991 | Wurster |
| 5,036,855 | A | 8/1991 | Fry |
| 5,080,101 | A | 1/1992 | Dory |
| 5,080,102 | A | 1/1992 | Dory |
| 5,080,660 | A | 1/1992 | Buelna |
| 5,117,832 | A | 6/1992 | Sanghvi |
| 5,234,429 | A | 8/1993 | Goldhaber |
| 5,271,402 | A | 12/1993 | Yeung |
| 5,391,140 | A | 2/1995 | Schaetzle |
| 5,441,499 | A | 8/1995 | Fritzsch |
| 5,471,988 | A | 12/1995 | Fujio |
| 5,474,071 | A | 12/1995 | Chapelon |
| 5,492,126 | A | 2/1996 | Hennige |
| 5,520,188 | A | 5/1996 | Hennige |
| 5,558,092 | A | 9/1996 | Unger |
| 5,619,999 | A | 4/1997 | Von Behren |
| 5,666,954 | A | 9/1997 | Chapelon |
| 5,720,287 | A | 2/1998 | Chapelon |
| 5,762,066 | A | 6/1998 | Law |
| 5,769,790 | A | 6/1998 | Watkins |
| 5,810,007 | A | 9/1998 | Holupka |
| 5,882,302 | A | 3/1999 | Driscoll, Jr. |
| 5,976,092 | A | 11/1999 | Chinn |
| 5,993,389 | A | 11/1999 | Driscoll, Jr. |
| 6,002,251 | A | 12/1999 | Sun |
| 6,007,499 | A | 12/1999 | Martin |
| 6,042,556 | A | 3/2000 | Beach |
| 6,050,943 | A | 4/2000 | Slayton |
| 6,083,159 | A | 7/2000 | Driscoll, Jr. |
| 6,126,607 | A | 10/2000 | Whitmore, III |
| 6,196,972 | B1 | 3/2001 | Moehring |
| 6,217,530 | B1 | 4/2001 | Martin |
| 6,254,601 | B1 | 7/2001 | Burbank |
| 6,267,734 | B1* | 7/2001 | Ishibashi et al. ............... 601/2 |
| 6,315,741 | B1 | 11/2001 | Martin |
| 6,390,973 | B1 | 5/2002 | Ouchi |
| 6,425,867 | B1 | 7/2002 | Vaezy |
| 6,432,067 | B1 | 8/2002 | Martin |
| 6,451,013 | B1 | 9/2002 | Bays |
| 6,461,314 | B1 | 10/2002 | Pant |
| 6,488,639 | B1 | 12/2002 | Ribault |
| 6,500,133 | B2 | 12/2002 | Martin |
| 6,508,774 | B1 | 1/2003 | Acker |
| 6,537,224 | B2 | 3/2003 | Mauchamp |
| 6,602,251 | B2 | 8/2003 | Burbank |
| 6,613,004 | B1 | 9/2003 | Vitek |
| 6,626,855 | B1 | 9/2003 | Weng |
| 6,632,177 | B1* | 10/2003 | Phillips et al. ............... 600/458 |
| 6,633,658 | B1 | 10/2003 | Dabney |
| 6,645,162 | B2 | 11/2003 | Friedman |
| 6,666,835 | B2 | 12/2003 | Martin |
| 6,676,601 | B1 | 1/2004 | Lacoste |
| 6,692,450 | B1 | 2/2004 | Coleman |
| 6,716,184 | B2 | 4/2004 | Vaezy |
| 6,719,694 | B2 | 4/2004 | Weng |
| 6,740,082 | B2 | 5/2004 | Shadduck |
| 6,764,488 | B1 | 7/2004 | Burbank |
| 6,840,936 | B2 | 1/2005 | Sliwa, Jr. |
| 6,936,046 | B2 | 8/2005 | Hissong |
| 7,063,666 | B2 | 6/2006 | Weng |
| 7,105,007 | B2 | 9/2006 | Hibler |
| 7,175,596 | B2 | 2/2007 | Vitek |
| 7,258,674 | B2 | 8/2007 | Cribbs |
| 7,452,357 | B2 | 11/2008 | Voegele |
| 7,470,241 | B2 | 12/2008 | Weng |
| 7,473,224 | B2 | 1/2009 | Makin |
| 7,699,782 | B2 | 4/2010 | Angelsen |
| 2001/0012934 | A1 | 8/2001 | Chandrasekaran |
| 2001/0017848 | A1* | 8/2001 | Tiedemann, Jr. ............... 370/318 |
| 2002/0029036 | A1 | 3/2002 | Goble |
| 2002/0065512 | A1 | 5/2002 | Fjield |
| 2002/0120259 | A1 | 8/2002 | Lettice |
| 2003/0004439 | A1 | 1/2003 | Pant |
| 2003/0060736 | A1 | 3/2003 | Martin |
| 2003/0233045 | A1 | 12/2003 | Vaezy |
| 2004/0030269 | A1 | 2/2004 | Horn |
| 2004/0039312 | A1* | 2/2004 | Hillstead et al. ............... 601/2 |
| 2004/0082859 | A1 | 4/2004 | Schaer |
| 2004/0153126 | A1 | 8/2004 | Okai |
| 2004/0242999 | A1 | 12/2004 | Vitek |
| 2004/0243201 | A1 | 12/2004 | Goldman |
| 2005/0038340 | A1 | 2/2005 | Vaezy |
| 2005/0085726 | A1 | 4/2005 | Lacoste |
| 2005/0101854 | A1 | 5/2005 | Larson |
| 2005/0154431 | A1 | 7/2005 | Quistgaard |
| 2005/0203399 | A1 | 9/2005 | Vaezy |
| 2005/0256405 | A1 | 11/2005 | Makin |
| 2005/0267454 | A1 | 12/2005 | Hissong |
| 2006/0052701 | A1 | 3/2006 | Carter |
| 2006/0056273 | A1* | 3/2006 | Scoca et al. ............... 367/99 |
| 2006/0264748 | A1 | 11/2006 | Vaezy |
| 2007/0066990 | A1 | 3/2007 | Marsella |
| 2007/0194658 | A1 | 8/2007 | Zhang |
| 2007/0197918 | A1 | 8/2007 | Vitek |
| 2007/0238994 | A1 | 10/2007 | Stecco |
| 2008/0039724 | A1 | 2/2008 | Seip |
| 2008/0071165 | A1 | 3/2008 | Makin |
| 2008/0086036 | A1 | 4/2008 | Hartley |
| 2008/0125771 | A1 | 5/2008 | Lau |
| 2008/0217259 | A1* | 9/2008 | Siversson ............... 210/748 |
| 2008/0221647 | A1 | 9/2008 | Chamberland |
| 2008/0253525 | A1* | 10/2008 | Boyden et al. ............... 378/87 |
| 2008/0281314 | A1 | 11/2008 | Johnson |
| 2008/0319436 | A1 | 12/2008 | Daniel |
| 2009/0036774 | A1 | 2/2009 | Weng |
| 2009/0228001 | A1 | 9/2009 | Pacey |
| 2009/0326420 | A1 | 12/2009 | Moonen |

FOREIGN PATENT DOCUMENTS

| | | |
|---|---|---|
| EP | 0614651 A1 | 9/1994 |
| EP | 0734742 A2 | 10/1996 |
| EP | 1 726267 A2 | 11/2006 |
| GB | 2 279 742 A | 1/1995 |
| JP | 405023336 A | 2/1993 |
| WO | 93/17646 A2 | 9/1993 |
| WO | 94/27502 A1 | 12/1994 |
| WO | 95/20360 A1 | 8/1995 |
| WO | 97/00646 A1 | 1/1997 |
| WO | 01/71380 A2 | 9/2001 |
| WO | 01/82777 A2 | 11/2001 |
| WO | 2004/073524 A1 | 9/2004 |
| WO | 2005/000097 A2 | 1/2005 |
| WO | 2006097661 A1 | 9/2006 |

OTHER PUBLICATIONS

Annex to Form PCT/ISA/206, Communication Relating to the Results of the Partial International Search mailed Dec. 15, 2009, in corresponding International Application No. PCT/US2009/053050, filed Aug. 6, 2009.

International Search Report dated Jun. 26, 2009, in International Application No. PCT/US2008/082829, filed Nov. 7, 2008.

Daum, D.R., and K. Hynynen, "A 256-Element Ultrasonic Phased Array System for the Treatment of Large Volumes of Deep Seated Tissue," IEEE Transactions on Ultrasonics, Ferroelectrics, and Frequency Control 46(5):1254-1268, Sep. 1999.

Enholm, J.K., et al., "Improved Volumetric MR-HIFU Ablation by Robust Binary Feedback Control," IEEE Transactions on Biomedical Engineering 57(1):103-113, Jan. 2010.

Mougenot, C., et al., "Automatic Spatial and Temporal Temperature Control for MR-Guided Focused Ultrasound Using Fast 3D MR Thermometry and Multispiral Trajectory of the Focal Point," Magnetic Resonance in Medicine 52(5):1005-1015, Nov. 2004.

Mougenot, C., et al., "Three-Dimensional Spatial and Temporal Temperature Control With MR Thermometry-Guided Focused Ultrasound (MRgHIFU)," Magnetic Resonance in Medicine 61(3):603-614, Mar. 2009.

Ngo, F.C., et al., "An Experimental Analysis of a Sector-Vortex Phased Array Prototype," Proceedings of the IEEE Ultrasonics Symposium, Montreal, Oct. 3-6, 1989, vol. 2, pp. 999-1002.

Rabkin, B.A., et al., "Hyperecho in Ultrasound Images of HIFU Therapy: Involvement of Cavitation," Ultrasound in Medicine & Biology 31(7):947-956, Jul. 2005.

Umemura, S.-I., and C.A. Cain, "Acoustical Evaluation of a Prototype Sector-Vortex Phased-Array Applicator," IEEE Transactions on Ultrasonics, Ferroelectrics, and Frequency Control 39(1):32-38, Jan. 1992.

Extended European Search Report mailed Feb. 26, 2010, issued in European Patent Application No. 07811847.8, filed Apr. 13, 2007, 7 pages.

International Search Report mailed May 11, 2010, issued in International Application No. PCT/US2009/059589, filed Oct. 5, 2009, 5 pages.

International Search Report and Written Opinion mailed Oct. 26, 2010, issued in International Application No. PCT/US2010/026565, filed Mar. 8, 2010, 10 pages.

Cain, C.A., and S.-I. Umemura, "Concentric-Ring and Sector-Vortex Phased-Array Applicators for Ultrasound Hyperthermia," IEEE Transactions on Microwave Theory and Techniques 34(5):542-551, May 1986.

Chapelon, J.Y., et al., "The Feasibility of Tissue Ablation Using High Intensity Electronically Focused Ultrasound," Proceedings of the IEEE Ultrasonics Symposium 1993, Baltimore, Oct. 31-Nov. 3, 1993, pp. 1211-1214.

Chen, L., et al., "Effect of Blood Perfusion on the Ablation of Liver Parenchyma With High-Intensity Focused Ultrasound," Physics in Medicine and Biology 38(11):1661-1673, Nov. 1993.

Cheng, S.-Q., et al., "High-Intensity Focused Ultrasound in the Treatment of Experimental Liver Tumour," Journal of Cancer Research and Clinical Oncology 123(4):219-223, Apr. 1997.

Coad, J.E., "Thermal Fixation: A Central Outcome of Hyperthermic Therapies," Proceedings of the SPIE Conference on Thermal Treatment of Tissue: Energy Delivery and Assessment III 5698:15-22, San Jose, Calif., Jan. 23, 2005.

Delon-Martin, C., et al., "Venous Thrombosis Generation by Means of High-Intensity Focused Ultrasound," Ultrasound in Medicine & Biology 21(1):113-119, 1995.

Friedland, F., "Ultrasonic Therapy," American Journal of Nursing 59(9):1272-1275, Sep. 1959.

Fry, F.J., "Recent Bioeffects With Ultrasound on the Reproductive System and Solid Tumors," Journal of the Acoustical Society of America 63(Suppl. 1):S13, May 1978.

Hallberg, L., et al., "Menstrual Blood Loss—A Population Study: Variation at Different Ages and Attempts to Define Normality," Acta Obstetricia et Gynecologica Scandinavica 45(3):320-351, 1966.

Lee, J.M., et al., "Comparison of Wet Radiofrequency Ablation With Dry Radiofrequency Ablation and Radiofrequency Ablation Using Hypertonic Saline Preinjection: Ex Vivo Bovine Liver," Korean Journal of Radiology 5(4):258-265, Dec. 2004.

Lee, J.M., et al., "Wet Radio-Frequency Ablation Using Multiple Electrodes: Comparative Study of Bipolar Versus Monopolar Modes in the Bovine Liver," European Journal of Radiology 54:408-417, Jun. 2005.

Orsini-Meinhard, K., "UW Tech-Transfer Program Putting Discoveries to Work," The Seattle Times, May 27, 2007, 8 pages.

Rabkin, B.A., et al., "Biological and Physical Mechanisms of HIFU-Induced Hyperecho in Ultrasound Images," Ultrasound in Medicine & Biology 32(11):1721-1729, Nov. 2006.

Sanghvi, N.T., et al., "High Intensity Focused Ultrasound (HIFU) for the Treatment of Rectal Tumors: A Feasibility Study," Proceedings of IEEE Ultrasonics Symposium 3:1895-1898, Cannes, France, Nov. 1-4, 1994.

"ThermoDox™ Animal Studies to Be Presented at 6th International Symposium on Therapeutic Ultrasound in Oxford, England," Aug. 30-Sep. 2, 2006, Celsion, Inc., <http://www.celsion.com/news/releasedetail.cfm> [retrieved Oct. 8, 2007], 2 pages.

"ThermoDox™: Heat-Activated Liposome Drug," © 2007 Celsion, Inc., <http://www.celsion.com/products/ThermoDox.cfm> [retrieved Oct. 8, 2007], 3 pages.

Vaezy, S., et al., "Image-Guided Acoustic Therapy," Annual Review of Biomedical Engineering 3:375-390, Aug. 2001.

Winter, T.C., et al., "Focal Tumor Ablation: A New Era in Cancer Therapy," Ultrasound Quarterly 22(3):204-209, Sep. 2006.

Zanelli, C.I., et al., "Design and Characterization of a 10 cm Annular Array Transducer for High Intensity Focused Ultrasound (HIFU) Applications," Proceedings of the IEEE Ultrasonics Symposium 3:1887-1890, Cannes, France, Nov. 1-4, 1994.

Mittleman, R.S., et al., "Use of the Saline Infusion Electrode Catheter for Improved Energy Delivery and Increased Lesion Size in Radiofrequency Catheter Ablation," Pacing and Clinical Electrophysiology 18(5, Pt. I):953-1081, May 1995.

* cited by examiner

OPTIMIZATION AND FEEDBACK CONTROL OF HIFU POWER DEPOSITION THROUGH THE FREQUENCY ANALYSIS OF BACKSCATTERED HIFU SIGNALS

BACKGROUND

As an alternative to more invasive types of surgical procedures, many physicians are employing the use of High Intensity Focused Ultrasound (HIFU) as a technique to therapeutically treat internal body tissues. With HIFU, an ultrasound signal of sufficient power (pressure and particle velocity) and time is focused on a target volume of tissue in order to change a state of the tissue by heating and/or by cavitation.

To be effective in treating tissue, the delivered energy of the HIFU signal must be sufficient to cause the desired physical effect. Additionally, the energy must not be so great or uncontrolled as to cause unintended collateral damage to healthy tissues surrounding the target volume. Due to the non-homogenous nature of tissue(s) in the body, variations in attenuation, propagation velocity, and acoustic impedance modify the expected acoustic wave propagation and deposition of HIFU energy delivered to a target tissue volume when compared to homogeneous material. The technology disclosed herein is a method and apparatus for dynamically controlling the level of energy in a HIFU signal and/or the location where the energy is directed so that the desired physical effect in tissue is obtained and collateral damage to surrounding tissue is minimized.

SUMMARY

As indicated above, the technology disclosed herein is a method and apparatus for optimizing and controlling the energy of a HIFU signal delivered by a transducer to a desired location, such as within the tissue of a patient, using the harmonic distortion that occurs in a high amplitude pressure waveform traveling through tissue.

A continuous wave (CW) or pulsed mode HIFU signal is focused on a target volume in the patient. In acoustics, energy or power at the fundamental frequency of the HIFU signal is converted to higher harmonics in regions of high pressure. In one embodiment, the power of the echo signals in one frequency range may be compared to the power of the echo signals in a second frequency range. The power in the received echoes as a function of frequency is determined using the Fourier transform or other signal processing method. This comparison is used to calculate K, which is the ratio of the power in the two frequency ranges. In one embodiment, the power in the harmonic content of the waveform is compared to the power in the fundamental frequency. In another embodiment, the power in the odd harmonics is compared to the power in the fundamental frequency. In yet another embodiment, the power in one group of frequencies is compared to the power in another group of frequencies, of which one may contain the fundamental frequency. In yet another embodiment, the phase difference for the harmonics can be used to calculate K.

The ratio K may be found for a multitude of spatial positions from the transducer. This may be accomplished through windowing of the received echoes from the tissue at a specific time and calculating the Fourier transform. The characteristic curve formed by the values of K as a function of spatial location may be compared to a baseline characteristic curve, and the excitation signal may be adjusted to optimize the HIFU energy delivered to the intended target volume.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of the disclosed technology will become more readily appreciated as the same become better understood by reference to the following detailed description, when taken in conjunction with the accompanying drawings, wherein.

DETAILED DESCRIPTION

Although the technology disclosed herein is described with respect to its currently preferred embodiments and the best mode known for practicing the technology, the description is not to be construed as limiting. The disclosure is directed to all new and non-obvious features and aspects of the disclosed embodiments either taken alone or in combination. As discussed above, the technology disclosed herein relates to techniques for adjusting the level of energy of a HIFU signal and/or the location at which the energy is delivered. For the purposes of this application, the energy of a HIFU signal may be characterized by its power, pressure or other related characteristic.

Figure 1:
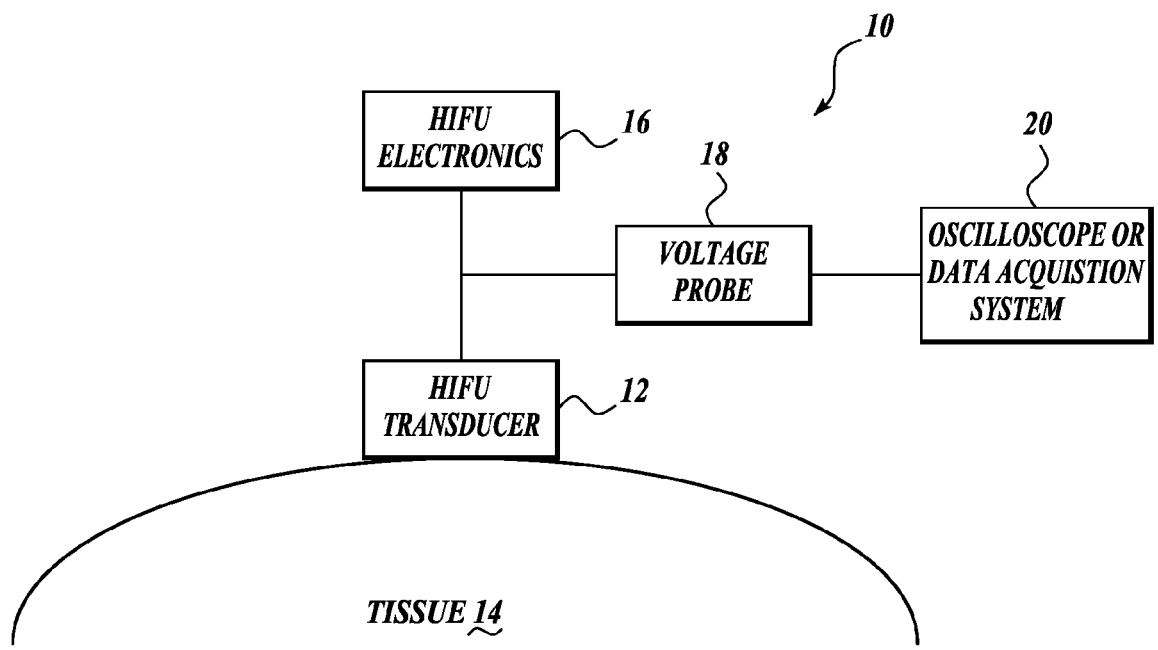
FIG. 1 illustrates a basic system for controlling the energy of a delivered HIFU signal, in accordance with an embodiment of the disclosed technology.

FIG. 1 shows a diagram of a system for adjusting the energy of a delivered HIFU signal in accordance with an embodiment of the disclosed technology. The system 10 includes a HIFU transducer 12 that delivers a HIFU signal to tissue 14 and HIFU electronics 16 that excites the transducer 12. A voltage probe 18 detects an electrical signal at the HIFU transducer 12. The system further includes an oscilloscope or other data acquisition system 20. In this case, an excitation signal from the HIFU electronics 16 stimulates the HIFU transducer 12 such that a high energy ultrasound signal is transmitted to the intended target in tissue 14. The energy in the HIFU signal is scattered, reflected, transmitted and absorbed as it propagates within the tissue. The absorbed energy is converted to heat and causes the temperature of the tissue to rise. The amount of energy absorbed depends on the pressure amplitude and frequency as well as the tissue characteristics. Typically, a HIFU device is designed such that the greatest pressure and absorption occur at the focus point of the device in the tissue. Energy of the signal that is not absorbed is either transmitted to deeper tissues or reflected and backscattered. It is the reflected and backscattered energy (ultrasound echoes) that can be detected and analyzed for harmonic distortion. Some of this backscattered acoustic energy is detected by the HIFU transducer 12 and converted into an electrical signal. The electrical signal is sensed using the voltage probe 18 and displayed/acquired on the oscilloscope or other data acquisition system 20.

Figure 2A:
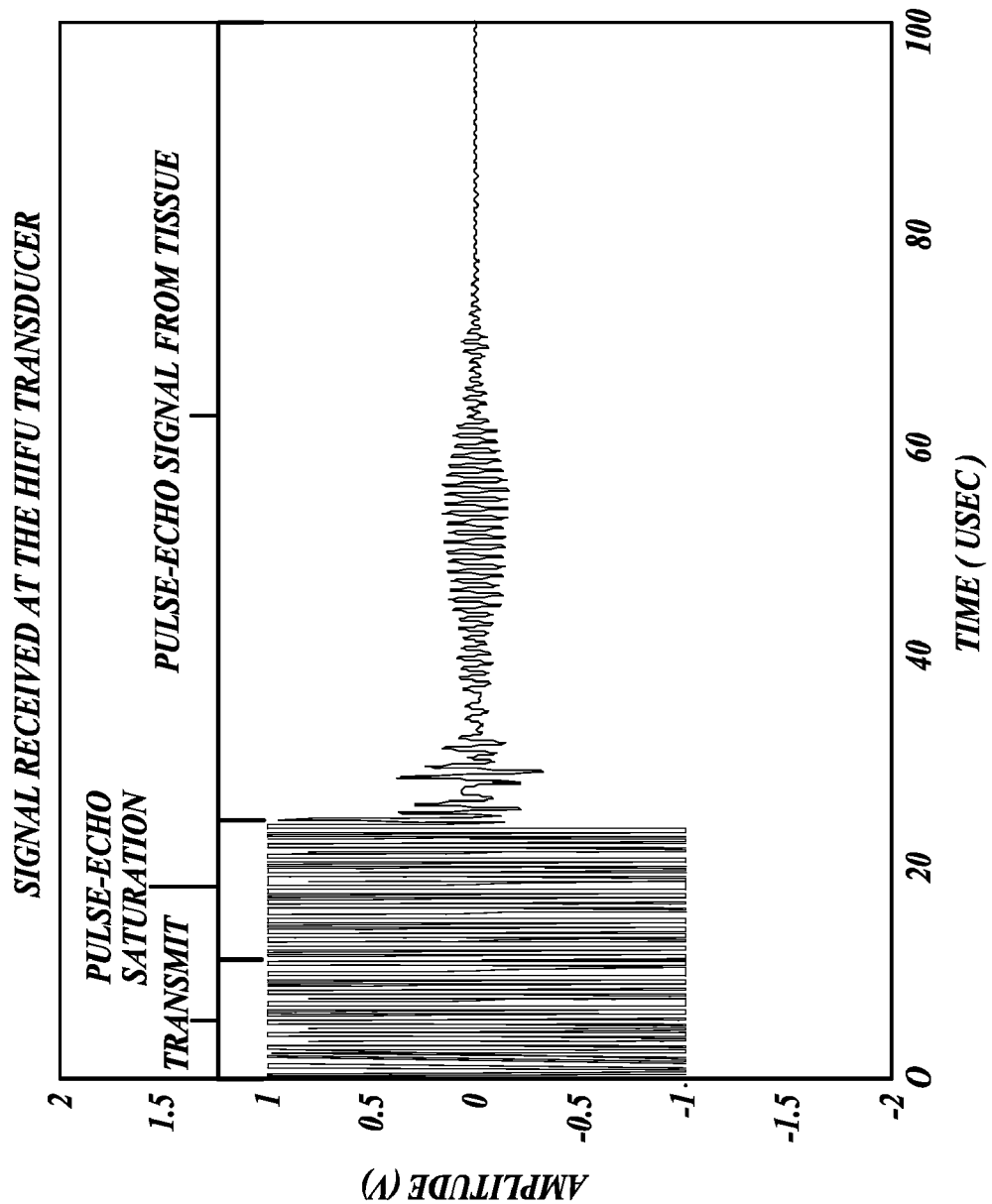
FIG. 2A shows a received echo as a function of time.
Figure 2B:
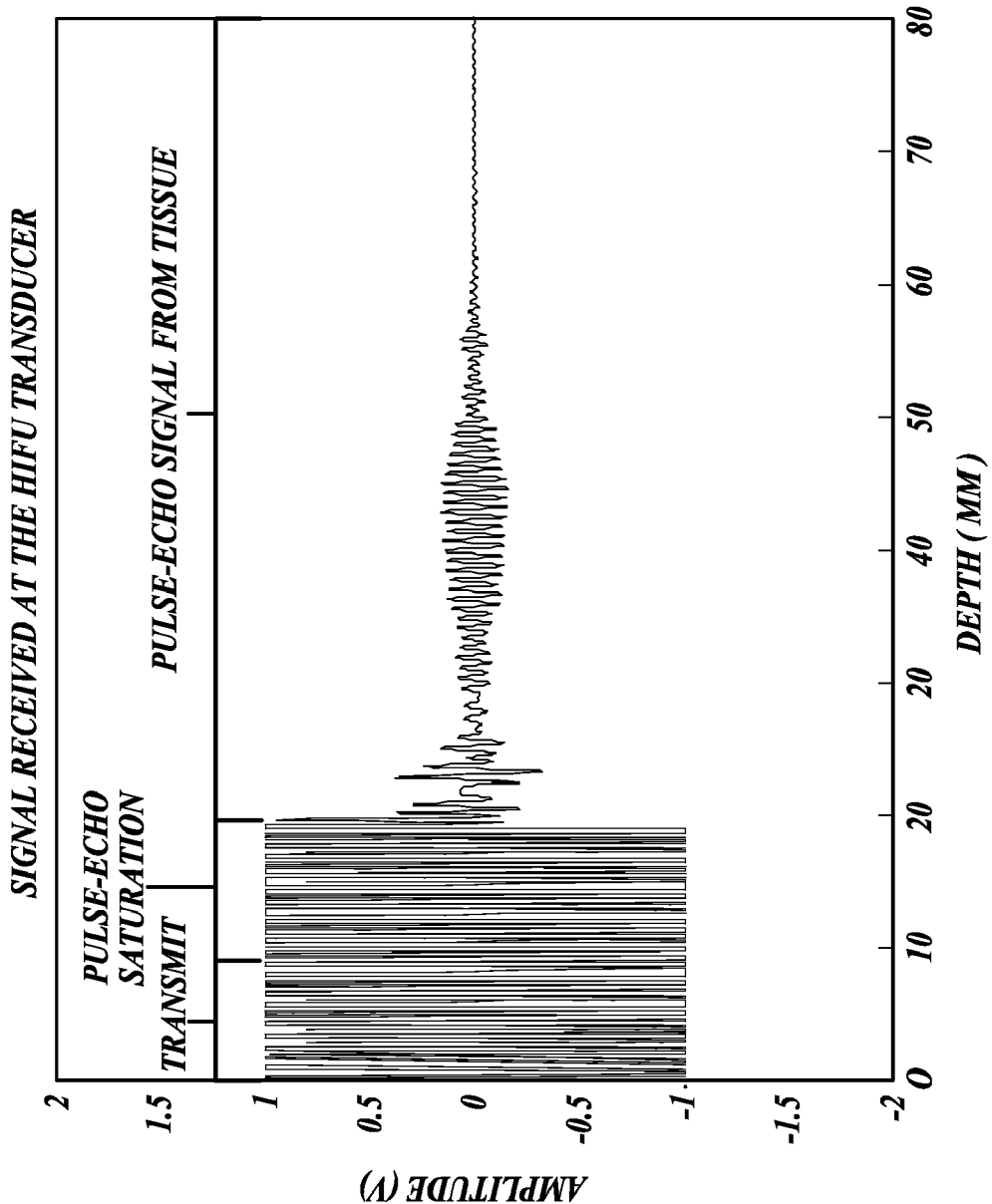
FIG. 2B shows a received echo as a function of distance.

FIG. 2A shows a representative signal captured at the data acquisition system 20 with three regions identified, namely transmit, pulse-echo saturation, and pulse-echo signal. For this example, the focal depth is 35 mm for the HIFU transducer. If it is assumed acquisition starts immediately when transmit begins, then the first detected signal will contain mostly information from the transmit pulse (transmit region). After transmit ends, it is expected that some of the first few echoes may cause clipping in the detection system (pulse-echo saturation). The issues with pulse-echo saturation may be mitigated by properly designing the detection circuit to ensure satisfactory dynamic range and bandwidth (e.g. time-gain control). After the initial large amplitude echoes have been received, the echoes from the tissue may be detected without any additional distortion added from the detection system (pulse-echo signal). Since in the embodiment shown, the HIFU transducer and detection transducer are the same, the time axis also represents depth through knowledge of the propagation velocity in the tissue as shown in FIG. 2B.

Figure 3:
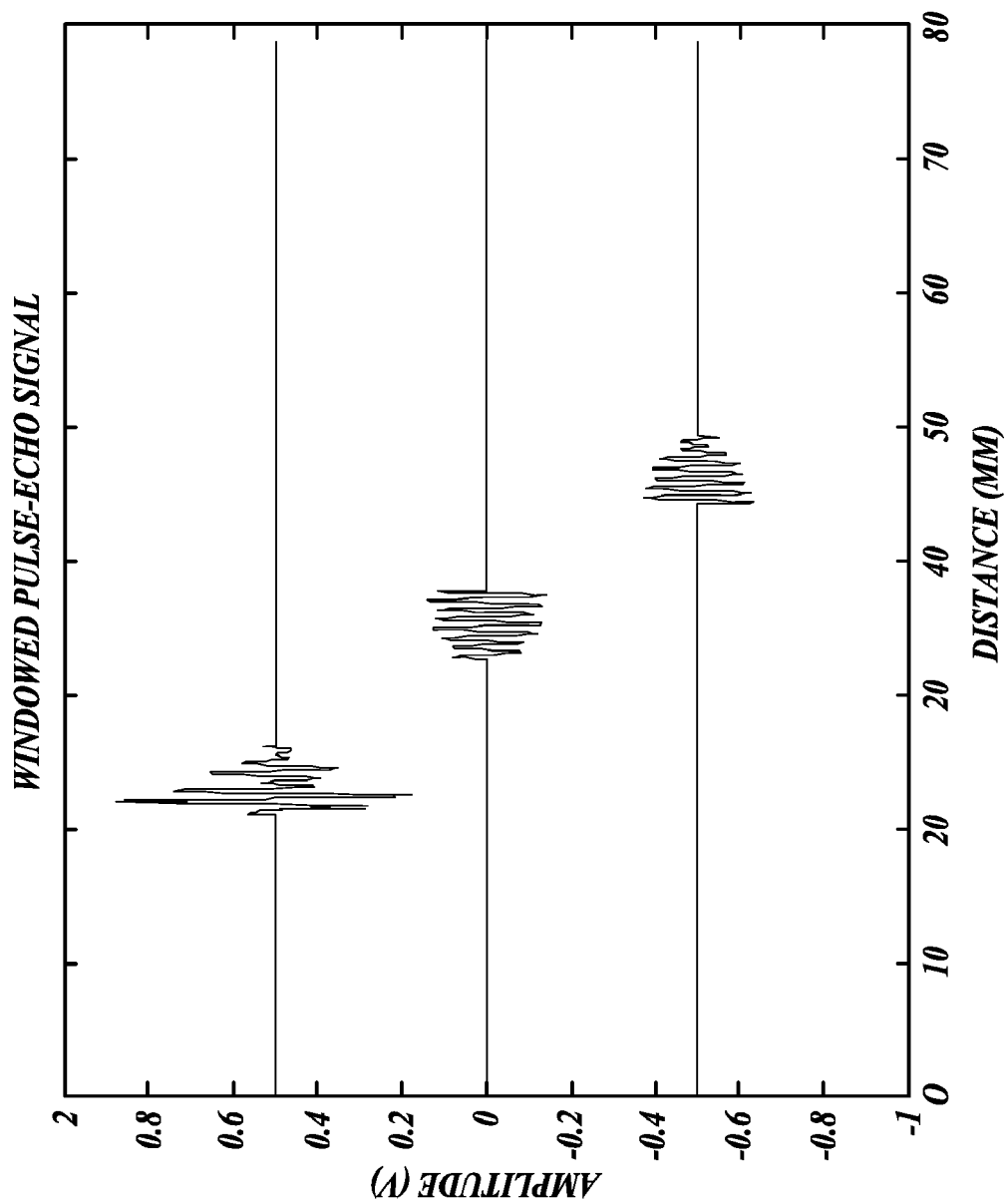
FIG. 3 shows windowed sections of a received echo at three different distances.
Figure 4:
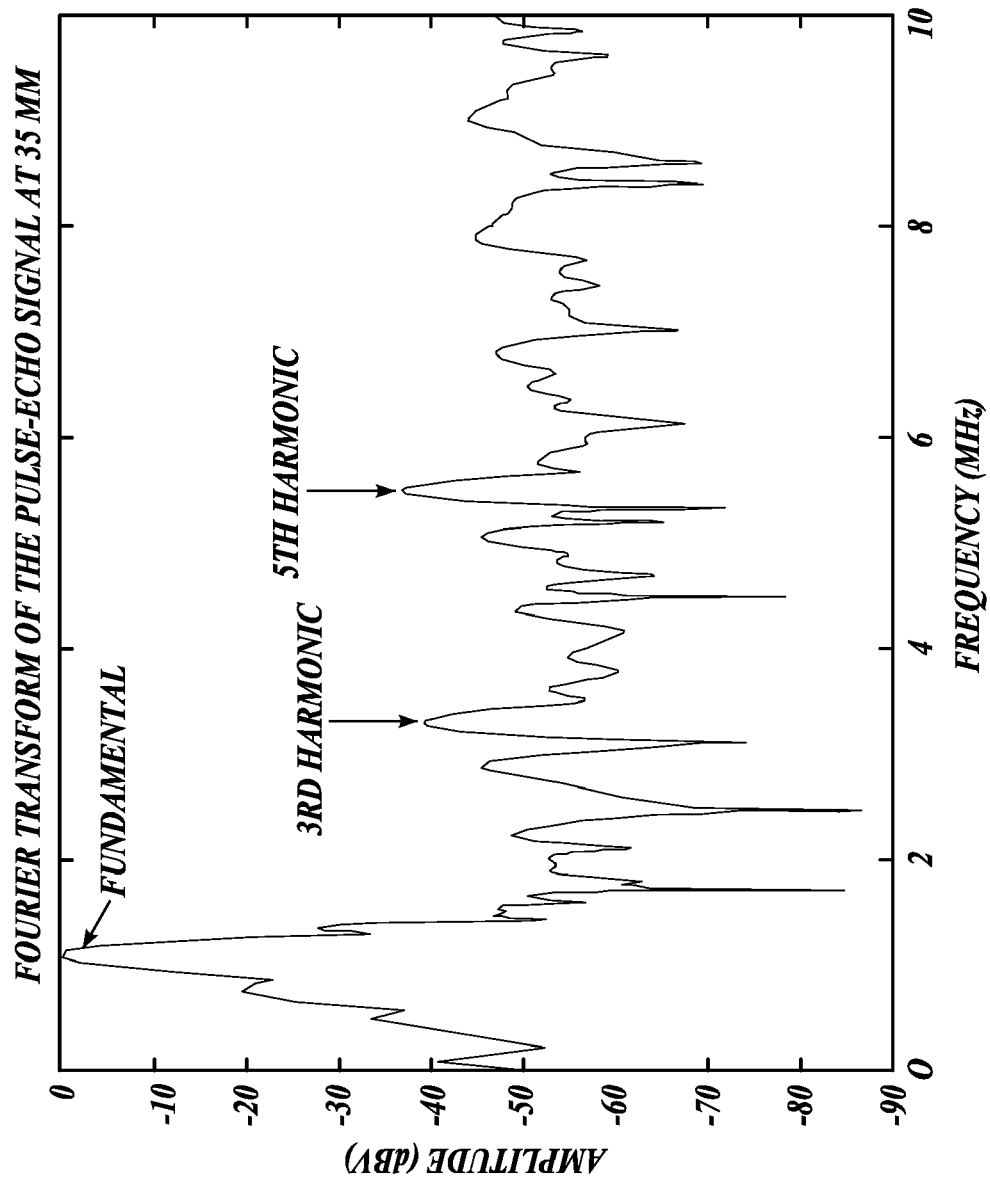
FIG. 4 shows the frequency spectrum of a windowed echo (distance of 35 mm) with the fundamental, 3rd and 5th harmonics identified.
Figure 5:
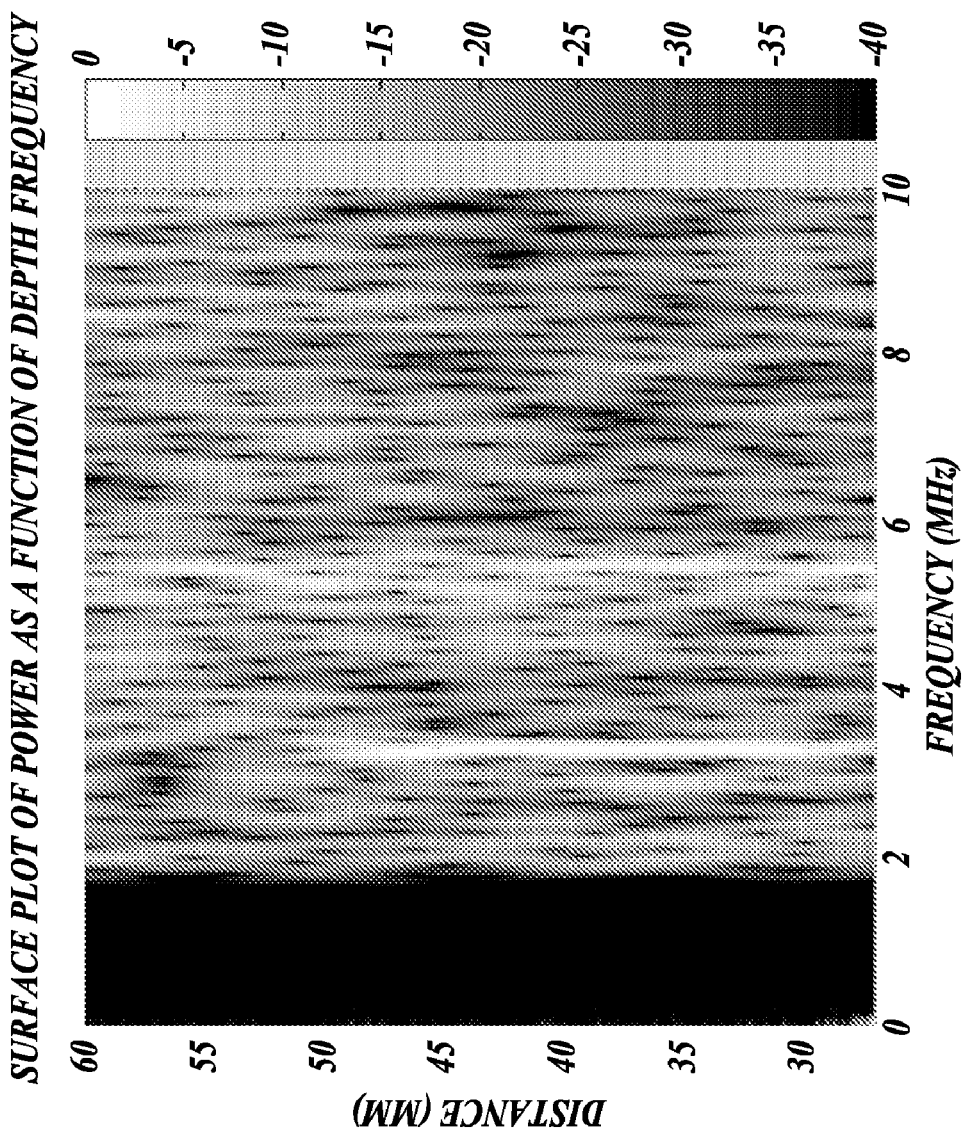
FIG. 5 shows a surface plot of the power in decibels as a function of frequency and distance mapped to a grayscale.

The energy of the echo signals as a function of frequency may be computed at different depths or spatial locations. In this case, the received echo signal is multiplied by a windowing function centered at a specific depth and the Fourier transform operator is applied. In the example shown in FIG. 3, echo signals are isolated at depths centered at 25, 35 and 45 mm with a rectangular function which is 5 mm in width. It is expected that the window width and amplitude will be adjusted to optimize the frequency representation of the echo signal. A Fourier transform of the echo signals at each depth signal is calculated to determine the energy of the echo signals as a function of frequency. FIG. 4 shows the frequency spectrum for the signal windowed at 35 mm. In this case, the fundamental frequency, $3^{rd}$ harmonic, and $5^{th}$ harmonic are identified. The even harmonics are typically not as easy to detect due to therapy transducer limitations. Although only three depths are shown in FIG. 3, the window function can run along the entire length of the pulse-echo signal or vector. In this case, a matrix of data is computed such that one axis is depth and the other axis is frequency. FIG. 5 shows a three dimensional surface plot in grayscale of a continuous analysis along the depth dimension. In this representation, the fundamental frequency of 1.1 MHz has been removed using a digital filter, which highlights the harmonics seen at 3.3 MHz and 5.5 MHz.

The Fourier transform determines the energy that occurs in frequency bins. Therefore, the energy in a particular frequency bin may be compared to other frequency bins or the energy over multiple frequency bins may be summed and compared. For example, frequencies around the fundamental frequency (e.g. bandwidth) may be a better representation of the power. EQUATIONS 1A and 1B show two different cases for calculating a ratio K, of the energy as represented by the power in two different frequencies or frequency ranges.

As with many signal processing schemes, signal conditioning may be required to detect and properly represent the power of the echo signals at the various frequencies. For example, the sensitivity of the detection transducer or attenuation as a function of frequency and depth may need to be introduced to fully appreciate differences in the energy at the various frequencies in tissue.

$$K_{f1f0}(r) = \frac{P(f_1, r)}{P(f_0, r)} \quad (1A)$$

$$K_{f1f0}(r) = \frac{\sum_{f=f_1-\Delta f}^{f_1+\Delta f} P(f, r)}{\sum_{f=f_0-\Delta f}^{f_0+\Delta f} P(f, r)} \quad (1B)$$

FIG. 5 shows that the K values can be calculated as a function of spatial position or depth; therefore, K is a function of r or spatial distance. It is important to note that the calculation may include one frequency or multiple frequencies. For example, the K value may represent the power in the harmonics compared to the power in the fundamental.

Figure 6:
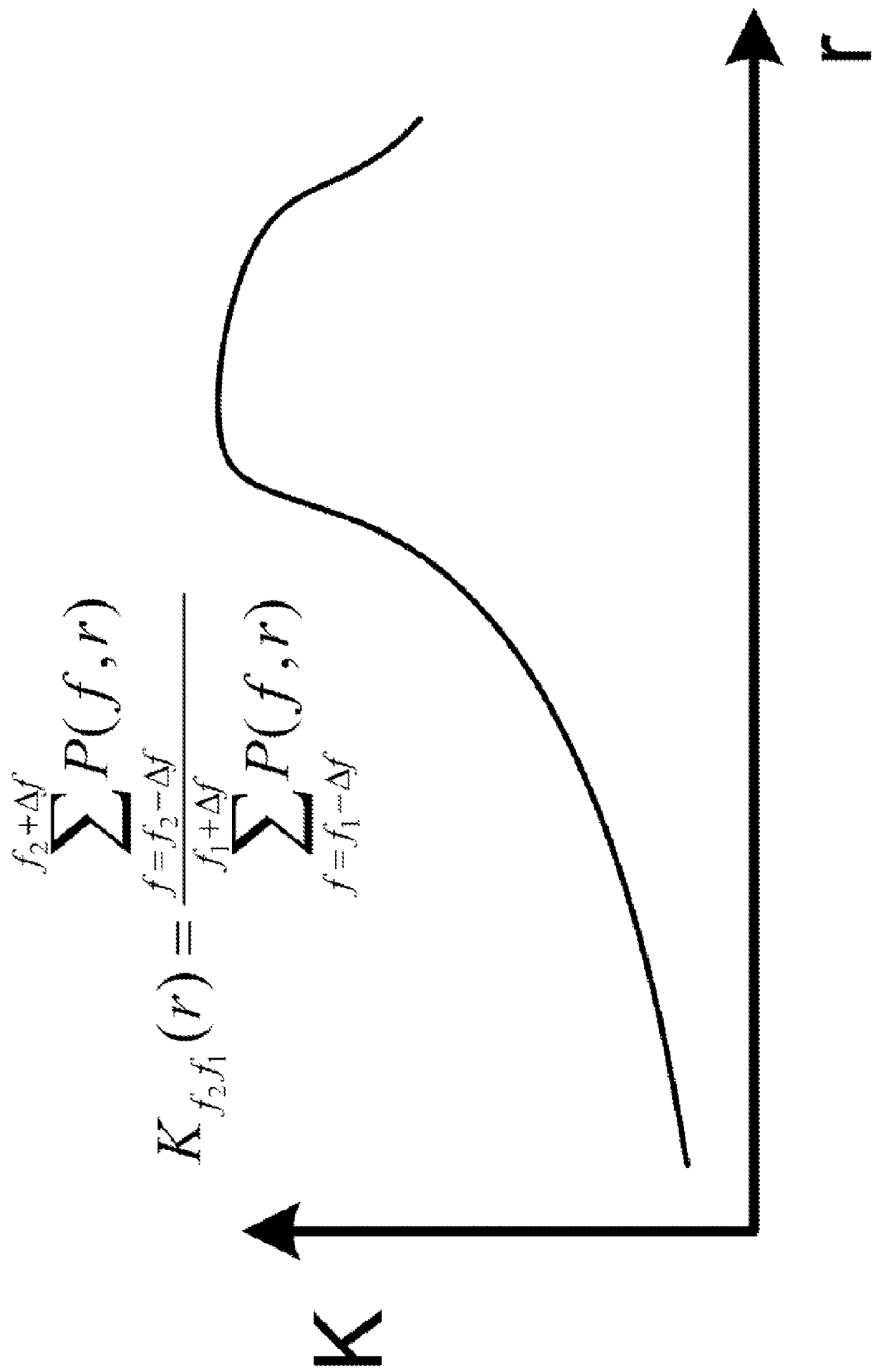
FIG. 6 shows an expected K value curve as a function of distance 'r'.

FIG. 6 shows an example of how the K values are expected to vary as a function of depth. In this example, the power around the fundamental is compared to the power in the harmonics. As can be seen, the ratio K has a maximum at or adjacent the focal point of the HIFU signal and then decreases with increasing distance away from the transducer.

Figure 7A:
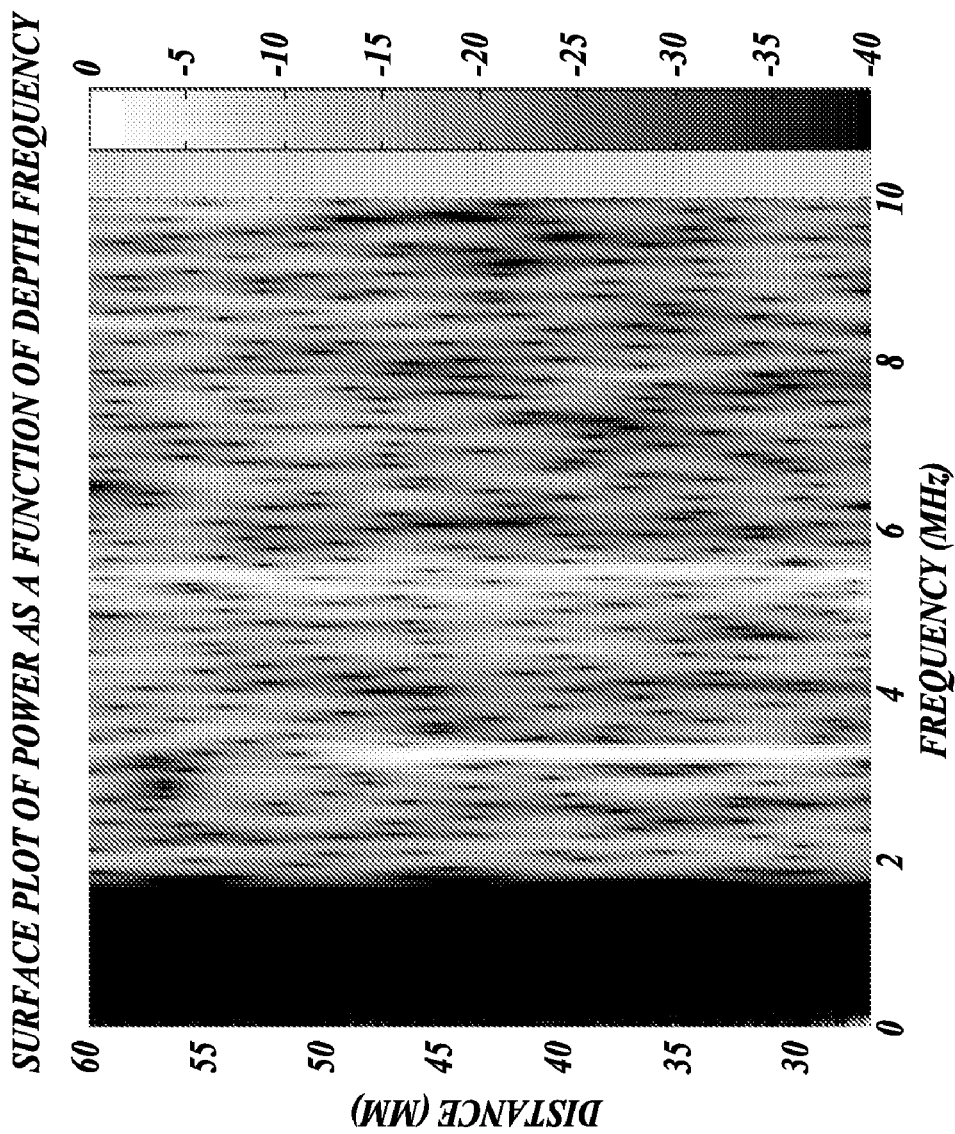
FIGS. 7A-7C show a surface plot of the power in decibels as a function of frequency and depth taken at three different times, t0, t1 and t2.
Figure 7B:
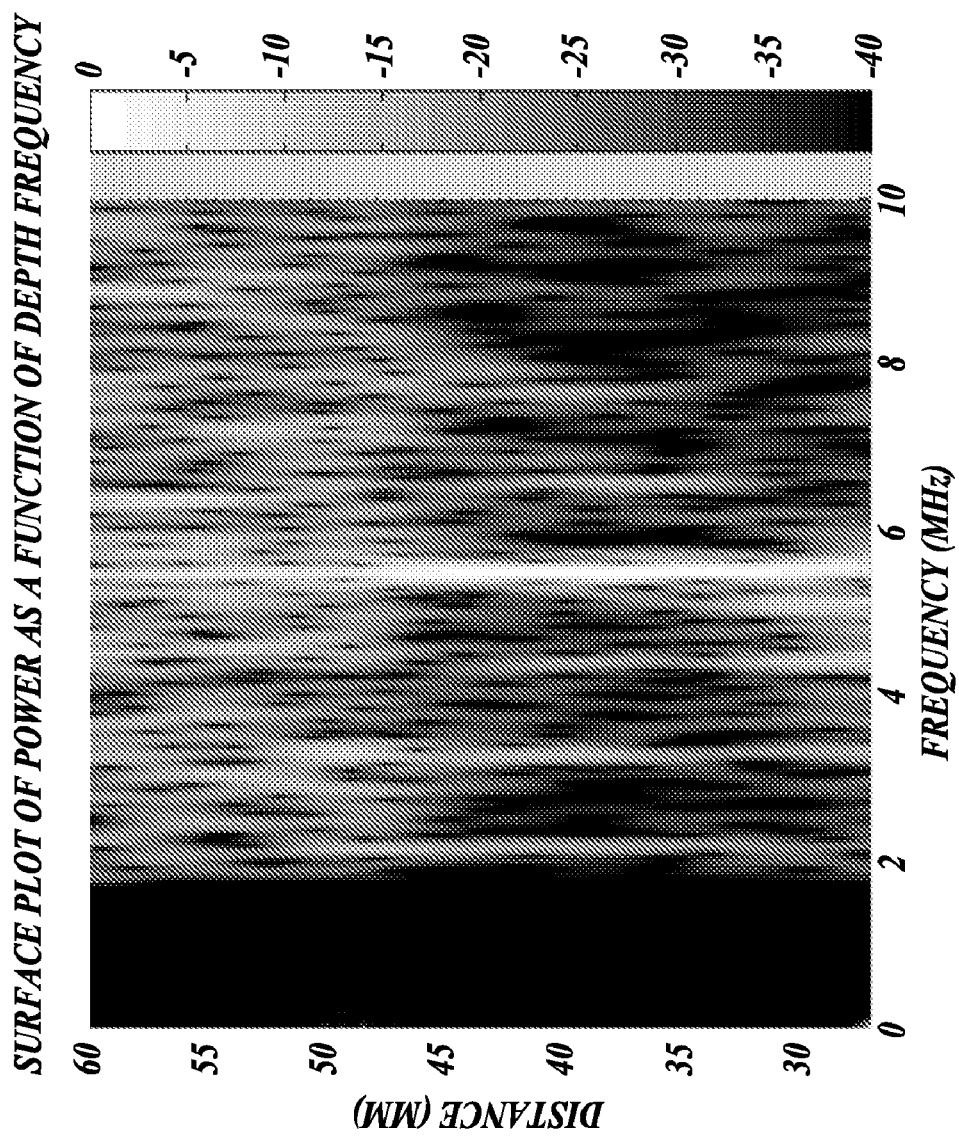
Figure 7C:
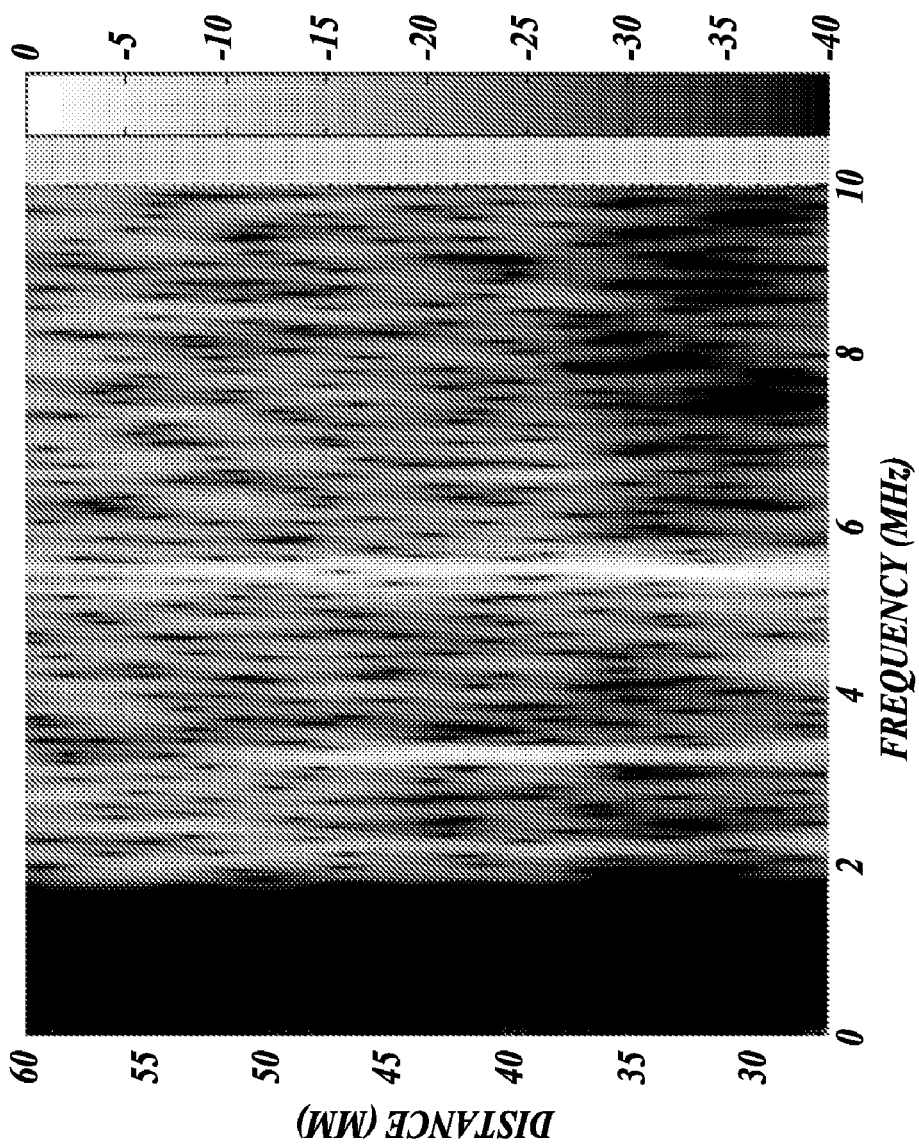

As described, it is possible to map the power as a function of frequency and spatial location for an echo. If the excitation level at the transducer is modified, then it is also possible to compare K values for different HIFU transducer pressures. The echoes are also available at different sampling intervals (pulse repetition interval). For example, if a pulse mode HIFU excitation is used, then the echo may be detected and analyzed between the excitation signals. This allows the K values to be compared for multiple excitation levels and/or multiple times. FIGS. 7A-7C show multiple surface plots that have been acquired from different echoes at times t0, t1 and t2. This may be due to variation in excitation level or just processing between excitation times. The frequency spectrum at each spatial location is calculated, and then K is calculated.

Figure 8:
FIG. 8 shows a graphical representation of K value matrices for different distances and acquisition times.
Figure 8:

FIG. 8 shows a representative format for storing K data in a computer memory. In one embodiment, the data is stored in a table 50 where one axis 52 is spatial location (depth) and another axis 54 is acquisition time. Each entry for a particular depth and time contains a matrix, e.g., 56, wherein the power ratio between two frequencies is calculated. In this representation, $K_{f2f0}$ is the power ratio in the third harmonic to the fundamental frequency. $K_{f2f1}$ is the power ratio in the third harmonic to the second harmonic. Since K is just a ratio of the power in two frequencies, $K_{f2f1}$ is simply the multiplicative inverse of $K_{f1f2}$. If it is necessary to compare the power in the fundamental to all harmonics, then essentially the column needs to be summed as set forth in EQUATION 2.

$$K_{total}(r_0,t_0) = K_{f1f0}(r_0,t_0) + K_{f2f0}(r_0,t_0) + K_{f3f0}(r_0,t_0) + \ldots + K_{fNf0}(r_0,t_0) \quad (2)$$

FIG. 8 also shows that the K values may be calculated at different excitation times t0, t1, t2, etc. By comparing the K values at these times (note: the excitation may vary at these different times) between each other or to a baseline, the approximate location of the focus may be determined as well as an estimate of the energy of the HIFU signal delivered to the tissue. For instance, if the characteristic curve formed by K as a function of spatial location shows significantly higher ratios than the baseline curve, then the output energy (pressure) may be reduced. Similarly, if the characteristic curve formed by K as a function of spatial location shows significantly lower ratios (or flatter) than the baseline curve, then the output energy may be increased. It is also possible to show harmonic saturation (maximum value for the ratio K) by graphing the K value as a function of the excitation amplitude for a particular depth.

If the excitation level is constant during the treatment, the amount of harmonics and location may suggest the amount of heating occurring throughout the tissue. This would help determine a limit to the amount of energy delivered to the intended target.

It should be also noted that although the power spectrum has been calculated at different depth and acquisition times, the phase may also be used to determine the amount of heating in tissue.

Since the K-value may be derived by the taking the Fourier transform of the echo signals, the power (energy per unit time) falling within each frequency bin as well as the phase is available for computation. The magnitude and phase in a particular frequency bin may be expressed in the following equation:

$$H(f_1) = A(f_1) * e^{-j2\pi\phi(f1)} \quad (3)$$

where $A(f_1)$ is the amplitude of the signal at frequency $f_1$ (the power is simply the square of A) and $\phi(f_1)$ is the phase of the signal at frequency $f_1$. Therefore, the phase difference between two frequency bins may be computed by taking the ratio of Equation 3 with the magnitude normalized to 1:

$$\epsilon_{f1f0} = \frac{e^{-j2\pi\varphi(f_1)}}{e^{-j2\pi\varphi(f_0)}} \quad (4)$$

Equation 4 may be rewritten as $$\epsilon_{f1f0} = e^{-j2\pi(\phi(f1)-\phi(f0))} \quad (5)$$

The argument in Equation 5 is the phase difference between the two signals. The phase difference as a function of depth at different excitation levels may also be used as a relative measure of energy in different frequencies or frequency bands, which in turn may be used to dynamically control the energy in the HIFU signal. For example, the magnitude of the phrase difference can be compared to a threshold previously known to relate the phase difference to delivered energy in the tissue. One or more characteristics of the HIFU signal can them be adjusted in accordance with the comparison.

Figure 9:
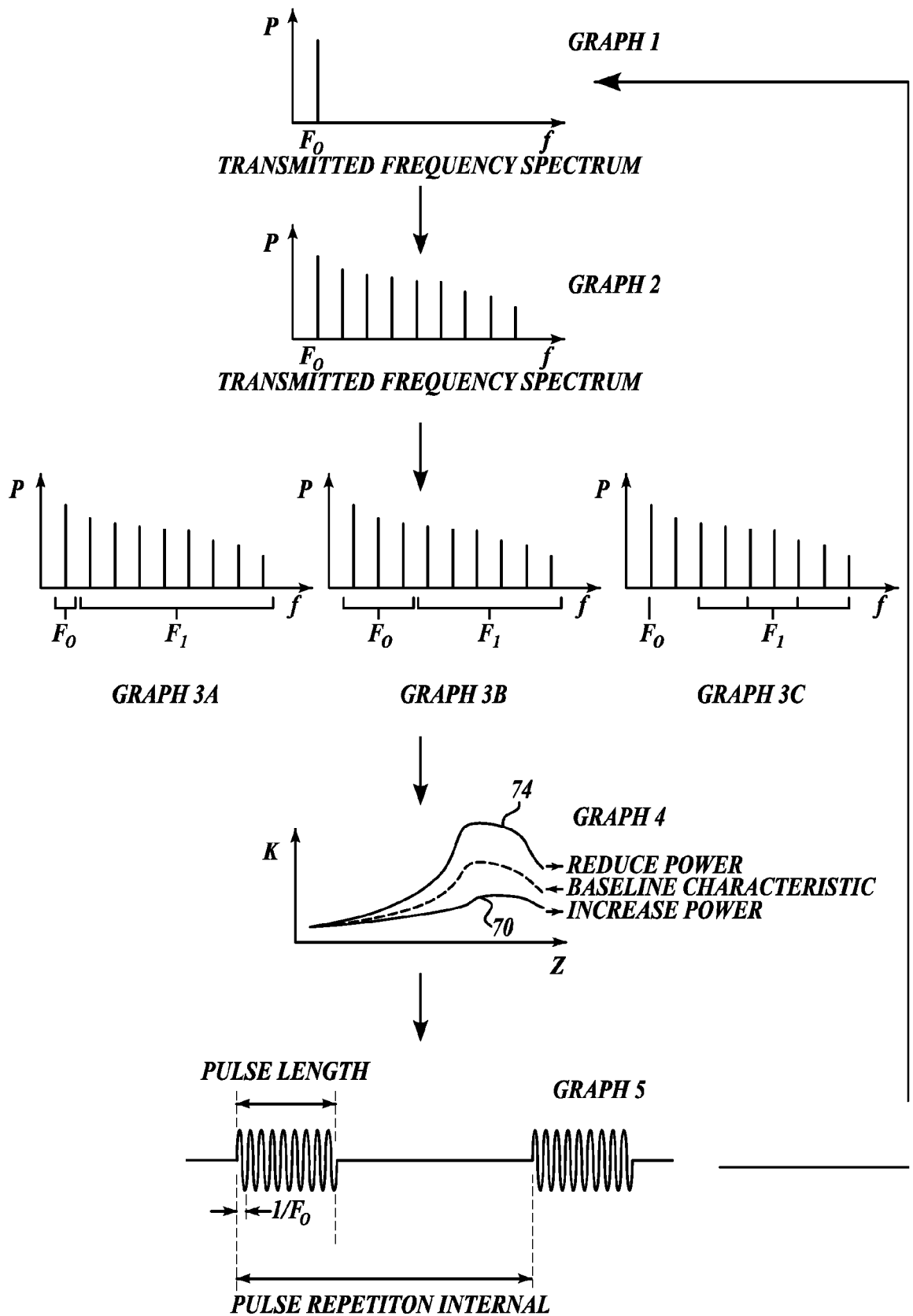
FIG. 9 shows a graphical representation of the steps performed to obtain K value curves and change the energy/power of a delivered HIFU signal in accordance with an embodiment of the disclosed technology.

FIG. 9 shows a summary of the basic steps to acquire the K values in accordance with one embodiment of the disclosed technology. First, the HIFU transducer is excited with a single frequency ($f_o$) as shown in graph 1. The HIFU signal may be a continuous wave (CW) or a pulsed sinusoid with a fundamental frequency $f_0$. In the case of CW, the pulse repetition interval is equal to the pulse length. As shown in graph 1, the HIFU excitation signal generated at the HIFU transducer probe has a signature spectrum where the energy of the frequency components that are different from the fundamental frequency of the HIFU signal, such as the harmonics or sub-harmonics, $f_1$, $f_2$, $f_3$, etc., are negligible compared with the energy of the fundamental frequency $f_0$. The high pressures created from the transmitted ultrasound signal converts the energy at the fundamental to harmonics and sub-harmonics in the tissue (graph 2). In particular, the energy of the signal at frequencies that are different from the fundamental frequency $f_0$ the HIFU signal (such as the frequency of one or more of the harmonics or sub-harmonics $f_1$, $f_2$, $f_3$, etc.) changes in comparison to the energy of the signal at the fundamental frequency $f_0$ as shown in graph 2. K values are calculated by combining the energies at these various frequencies as shown in graphs 3a, b and c. For example, the energy in one or more of the harmonics may be compared to the fundamental frequency. The energy in several lower order harmonics and the fundamental may be compared to that of the high frequency harmonics. Alternatively, the energy in the fundamental may only be compared to that of the higher order harmonics. These graphs by no means exhaust the possibilities of combining and comparing the energies at the various frequencies. As will be appreciated by those skilled in the art, the value of K may vary depending on the range of frequencies or particular harmonics or sub-harmonics used in computing the numerator and denominator.

Graph 4 shows that the K values may be graphed as a function of position. The ratio K may vary with the depth in the tissue as well as with different levels of transmit excitations. In one embodiment, the ratio K is expected to be a non-linear curve that increases with increasing depth in the tissue, but tends to reach a maximum at approximately the depth of the focal point of the HIFU signal. If K values are calculated after each transmit pulse (graph 5), then multiple K value curves may be generated as shown in graph 4.

Figure 10A:
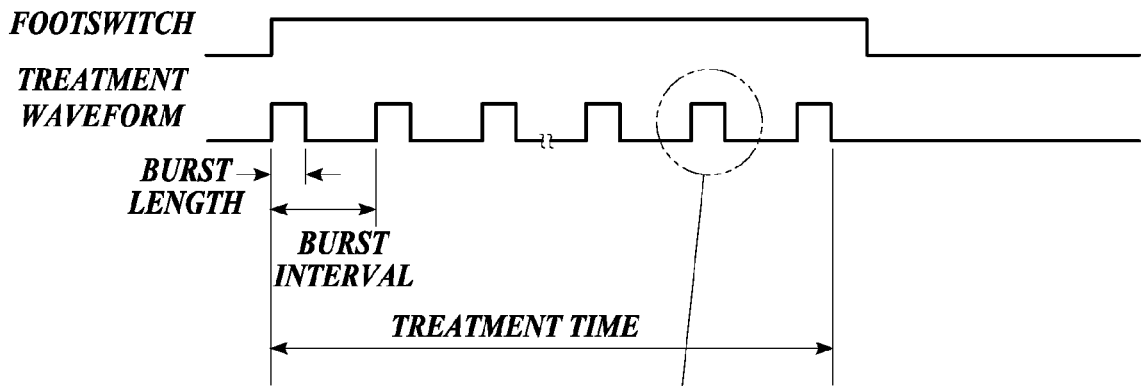
FIGS. 10A-10C illustrate the differences between burst length, burst interval, pulse length, and pulse rate interval of a pulsed HIFU signal.
Figure 10B:
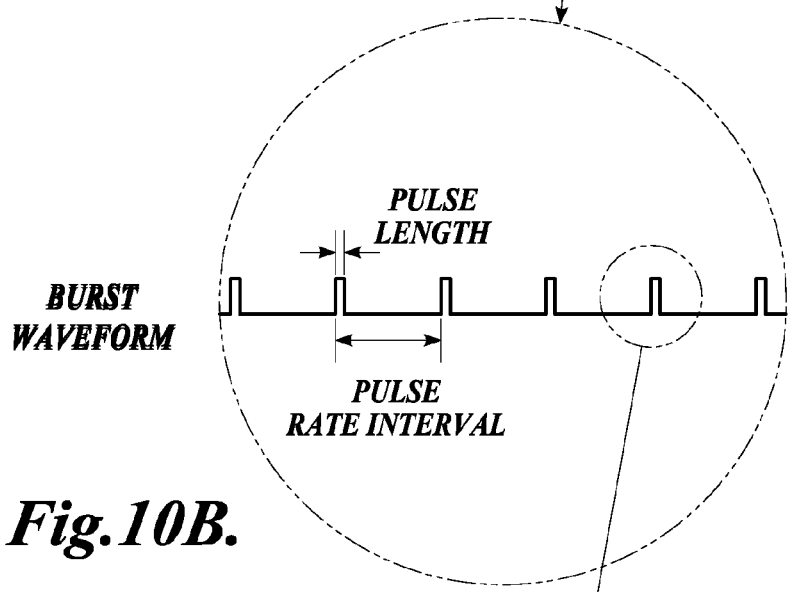
Figure 10C:
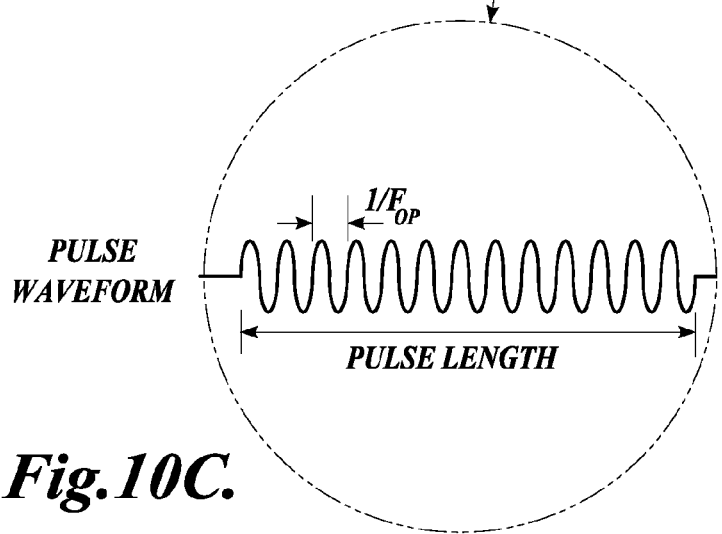

Graph 5 shows that the frequency of the transmit pulses may occur at the pulse repetition interval. FIGS. 10A-10C illustrate a pulse length and a pulse repetition interval in a burst. Many pulse lengths make up a burst. Each burst has a defined burst length, and the time between the start of each burst is the burst interval as shown in FIG. 10A. Each HIFU burst includes a number of HIFU pulses having a pulse length, where the time between the start of each pulse is the pulse rate interval as shown in FIG. 10B. The total time of the transmit excitation is the pulse length as shown in FIG. 10C. Each HIFU pulse is a sinusoidal waveform having a fundamental frequency $f_0$.

Returning to FIG. 9, a first curve 70 in graph 4 illustrates the ratio K for a first delivered energy level of the HIFU signal and a second curve 74 illustrates the ratio of K for a higher level of energy. By observing the changes in the K values as a function of depth, time, or transmit excitation, then a relative measure of the energy deposited spatially may be approximated.

The energy of the HIFU signal can be modified by increasing or decreasing any of the burst length, the burst interval, the pulse length, the pulse rate interval, or other characteristics such as the pulse amplitude. In the preferred embodiment, the HIFU treatment system automatically varies the acoustic output energy as a function of both the characteristic curve K relative to the baseline characteristic curve and whether the device is within an acceptable range for the values of K. An acceptable range for K may have an upper limit for pre-focal and focal values of K, based on safety levels.

Figure 11:
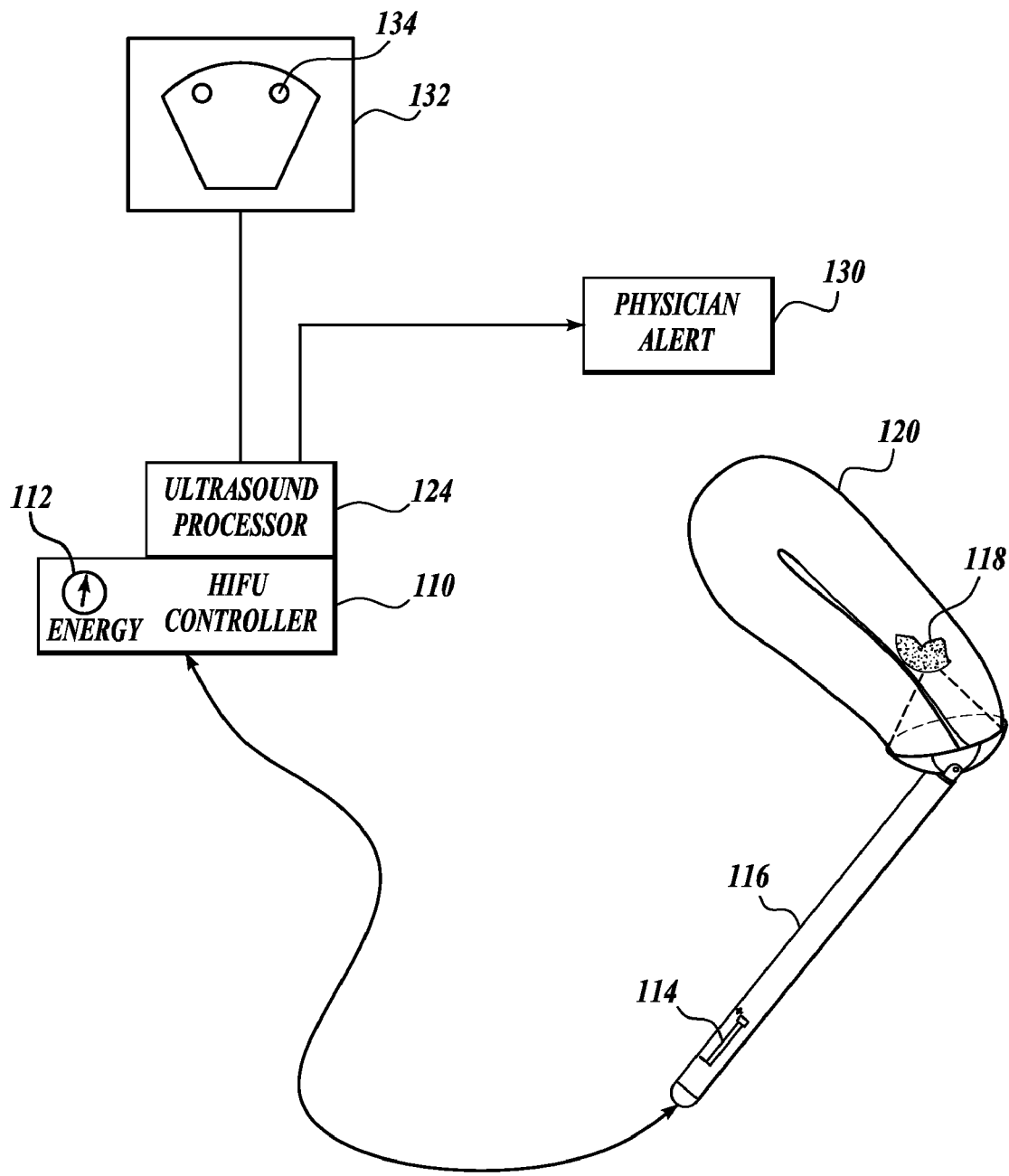
FIG. 11 illustrates an embodiment of a HIFU treatment system in which the disclosed technology can be implemented.

FIGS. 1 through 10 describe the disclosed technology starting with a simple block diagram. As one trained in the art will appreciate, there are other versions of this technology that generate similar benefits. FIG. 11 is another block diagram of a HIFU treatment system for implementing the technology disclosed herein. In the embodiment, a HIFU controller 110 delivers electronic driving signals to an external or internal transducer probe 116 that in turn converts the driving signals into acoustic HIFU signals. In FIG. 11, the HIFU transducer probe 116 is shown in a wand like apparatus. It is important to note that the HIFU transducer many have a plurality of elements in multiple dimensions that are mechanically or electronically steered to properly direct the ultrasound signal to the intended target. For example, the HIFU signals may be directed to a focal zone that is aimed at a target volume 118 through electronic or mechanical means. The target volume 118 may include all or a portion of a fibroid in a uterus 120. The HIFU signals create corresponding echo signals from tissue that are intercepted by the acoustic propagation. In most cases, the HIFU signal energy is concentrated on an axis that is located between the transducer probe 116 and the focal zone.

The echo signals are received by the transducer probe 116, converted into an electronic form and supplied to the HIFU controller 110. The detection of the echo signals may take place in the HIFU transducer or another specially designed device contained within the transducer probe 116. Furthermore, the detection device may be in a separate holder not contained within the transducer probe 116.

As previously described, the K values from the echo signals are calculated (FIG. 9), analyzed, and used to control one or more device parameters. An ultrasound processor 124 that is connected to or incorporated within the HIFU controller 110 analyzes the received echo signals and computes the K values. Based on the analysis, one or more characteristics of the HIFU excitation signal (e.g., peak power, average power, pulse duration, pulse repetition interval, etc.) are automatically or semi-automatically adjusted by the ultrasound processor 124. In some cases, the operator may be alerted via an audible, visible, or tactile alert 130 to manually adjust one of the device parameters through a control on the device (e.g., main console control 112, applicator, footswitch). A safety mechanism to ensure treatment does not continue without proper feedback signals may also be employed. In some instances, the system may also include ultrasound imaging capabilities that produce images of the tissue on a video display 132. The images may be obtained with a separate or integrated imaging ultrasound transducer. These images may be used to confirm proper adjustment of the HIFU excitation characteristics.

To estimate how much of the incident HIFU energy is being absorbed by the tissue at various positions at or adjacent to the focal point of the HIFU signal, the value of the ratio K is determined from the echo signals received from a given point in the tissue and compared to a desired value of K that was determined from prior testing. The value of the ratio K can therefore be used as a feedback signal to adjust one or more characteristics of the HIFU signal to affect absorption and hence HIFU effects on tissue at a given point. Detection of saturation (acoustic shock waves) or the slope of the increase in the K value as a function of the transmit excitation may also be used as feedback mechanisms to adjust one or more characteristics of the HIFU signal rather than depending on prior testing.

In one embodiment, if the determined value of K is below a threshold value for a particular position in the patient, then a signal characteristic such as the amplitude, peak or average power, duty cycle, pulse repetition rate, or other characteristic of the delivered HIFU signals can be electronically or manually increased to increase the ratio K at that position. Conversely, if the determined value of K is above a threshold, then one or more of the amplitude, power, duty cycle, pulse repetition rate, or other characteristic of the HIFU signal can be decreased to decrease the value of K. Different threshold values of K may be used to analyze echo signals received from within the target volume and outside that target volume in the body.

Figure 12A:
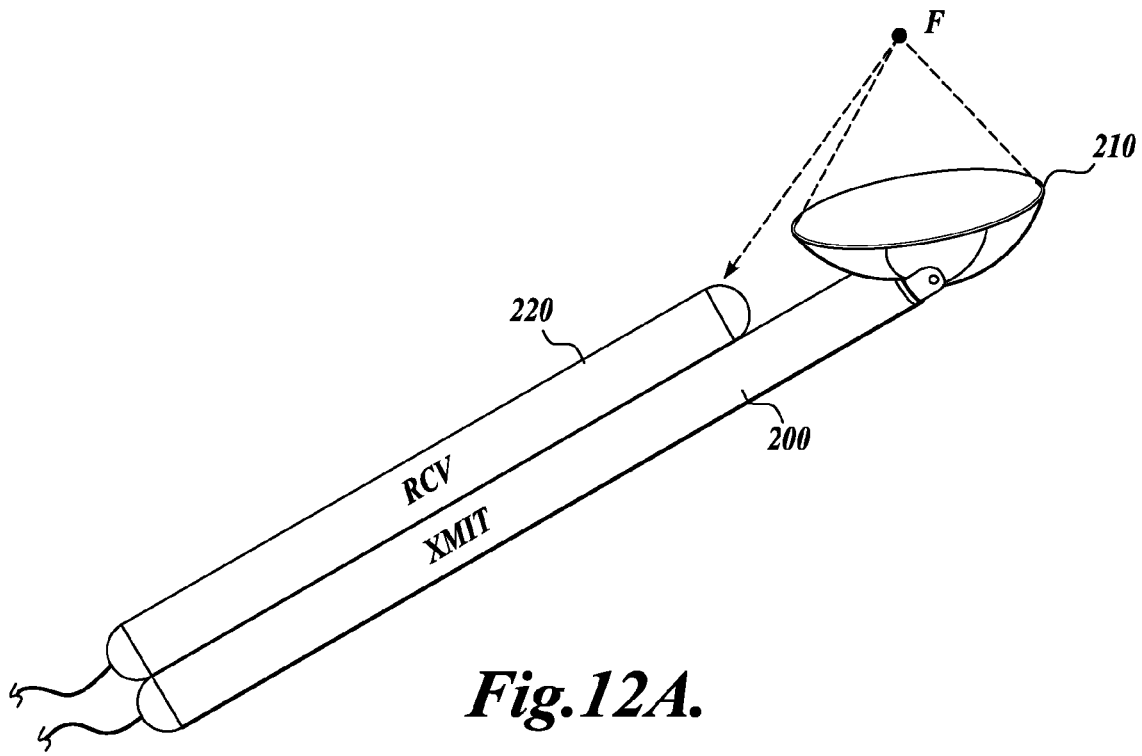
FIGS. 12A and 12B illustrate different types of transducer probes that transmit HIFU signals and receive echo signals from the patient.
Figure 12B:
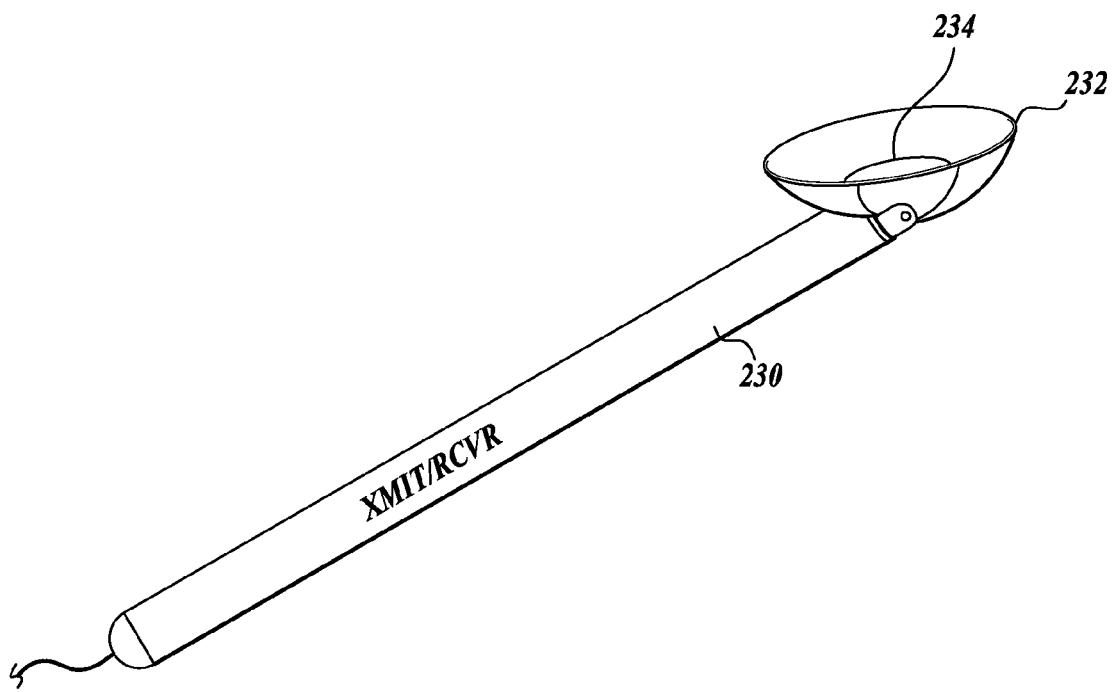

FIGS. 12A and 12B illustrate two possible applicator configurations that deliver HIFU signals to a target volume and detect echo signals at the fundamental frequency of the HIFU signal and at harmonics or sub-harmonics or other frequencies. In the example shown in FIG. 12A, a HIFU transducer probe 200 delivers one or more HIFU signals to a target volume. The HIFU transducer probe may have a fixed or variable focal point. Echo signals are received by a separate receiving transducer 220. The receiving transducer 220 has a bandwidth that is sufficient to detect echo signals over a range of frequencies that may include the fundamental frequency of the HIFU signals produced by the transducer probe 200 and its harmonics and sub-harmonics. The receiving transducer 220 may be an ultrasound imaging transducer, a non-imaging transducer such as a polyvinylidene fluoride (PVDF) transducer, a fiber optic hydrophone or other form of hydrophone.

In the example shown in FIG. 12B, a combination HIFU transmitting and receiving transducer probe 230 includes HIFU transmitting elements 232 that produce the HIFU signals and an array of higher bandwidth receiving elements 234 that are used to detect echo signals over a range of frequencies that may include the fundamental frequency of the HIFU signals and may also include one or more harmonics or sub-harmonics. The transducer in FIG. 12B may utilize a PVDF or other type of sensor.

Figure 13A:
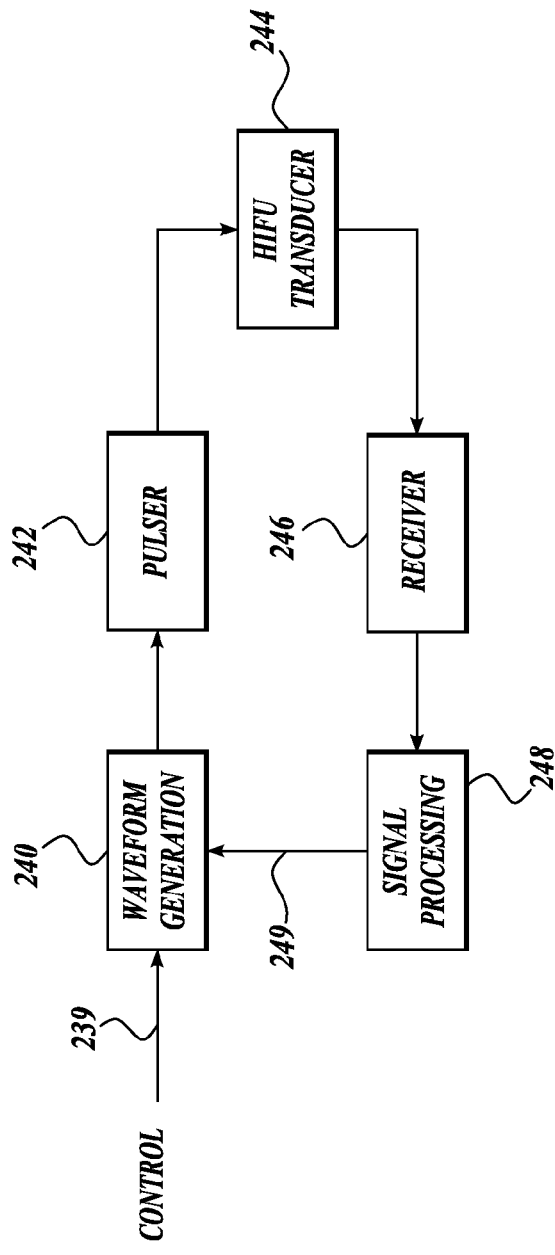
FIGS. 13A and 13B illustrate different feedback control systems to adjust the energy of a delivered HIFU signal.
Figure 13B:
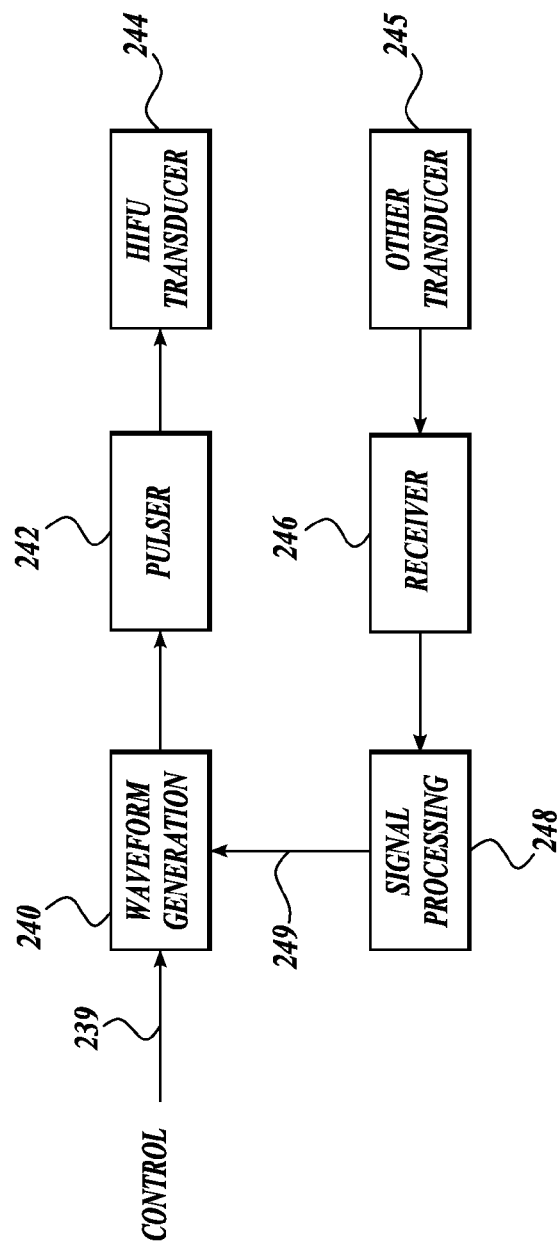

FIGS. 13A and 13B illustrate two different feedback mechanisms to adjust the energy of the HIFU signal delivered. In FIG. 13A, a control signal 239 from the HIFU controller 110 is applied to a waveform generator 240 to produce a waveform of the HIFU signals that will be applied to the patient. A control signal 249 is also applied to the waveform generator 240 by a signal processing unit 248 such as a programmable microprocessor or special purpose microprocessor within the ultrasound processor 224 that correlates the transmission and receipt of HIFU signals. Alternatively, the signal processing unit 248 may be a stand-alone device. The signals from the waveform generator 240 are supplied to a pulser 242 that increases the voltage of the signals to the level required by a HIFU transducer 244 to produce ultrasound acoustic signals. Echo signals are received by the HIFU transducer 244 where they are converted back into an electronic form for supply to a receiver 246. From the receiver 246, the echo signals are supplied to the signal processing unit 248 that analyzes the echo signals in accordance with the control to determine the ratio K described above. The signal processing unit 248 produces the control signal signals 249 that are fed back to the waveform generator 240 to electronically change one or more characteristics of the HIFU signals in order to change the energy of the HIFU signals delivered to the patient such that the detected ratio K falls within a desired range.

The feedback mechanism shown in FIG. 13B is similar to that shown in FIG. 13A except that a separate transducer 245 is used to detect the echo signals from the patient. For example, the transducer 245 may be a high bandwidth single element transducer such as a transducer with a PVDF material, or it may be an imaging transducer. Echo signals received by the transducer 245 are supplied to the receiver 246 and the signal processing unit 248 that determines the value of the ratio K and what, if any, characteristics of the HIFU signals should be electronically adjusted to control the energy of the HIFU signals delivered to the patient.

In yet another embodiment, the system includes an integrated or separate ultrasound imaging system that produces ultrasound images such as B-mode images of the tissue. The value of the ratio K is determined for various points in the body and is color coded or otherwise made visually distinct. The visually distinguished K values in the tissue can then be combined with a B-mode or other type of ultrasound image. In one embodiment, the color coded K values 134 are overlaid onto a B-mode image on the display 132 as shown in FIG. 11. By viewing the various levels of K, the physician can see where the higher frequency components of the HIFU signals are being delivered. The physician can then adjust the position of the HIFU transducer probe so that the HIFU signals are being delivered into the desired area. In addition or alternatively, the physician can see if one or more characteristics of the HIFU signals should be adjusted to change the amount of energy delivered to the patient.

In another embodiment, the system may calculate the center of mass, also called a centroid, for use in the physician's on-screen display, by analyzing the harmonics or sub-harmonics received by the system. This reduces the overall clutter in the on-screen display.

In another embodiment, the system records the value of the inputs that provide the K ratio value. This allows the system to detect a correlation between pulses in order to build a successive picture of trends in feedback characteristics. This may, for example, provide information valuable in determining whether cavitation or other tissue characteristics have occurred. The system may also make use of pulse inversion in order to create a data set of K ratio values over time for use in feedback analysis that eliminates the fundamental.

Figure 14:
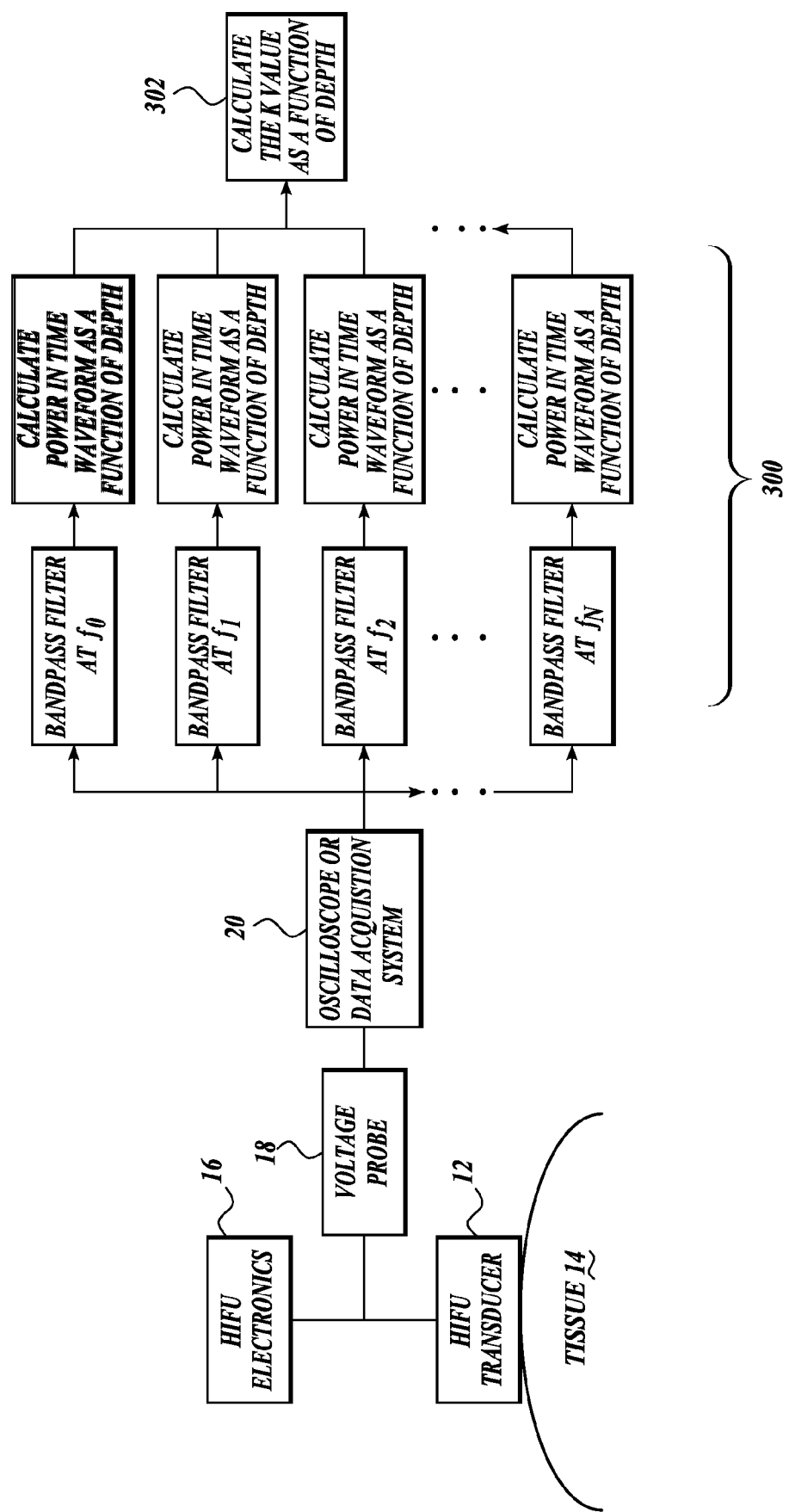
FIG. 14 illustrates a system for adjusting the delivered energy of a HIFU signal in accordance with another embodiment of the disclosed technology.

FIG. 14 illustrates another embodiment of the disclosed technology where instead of calculating the value K by Fourier transform, a number of filters 300 detect the energy of the echo signals in various frequency ranges. The filters can be digital (e.g., FIR or IIR) or analog (e.g., bandpass, notch, etc.). The value K can then be determined digitally or with an analog circuit 302.

Figure 15:
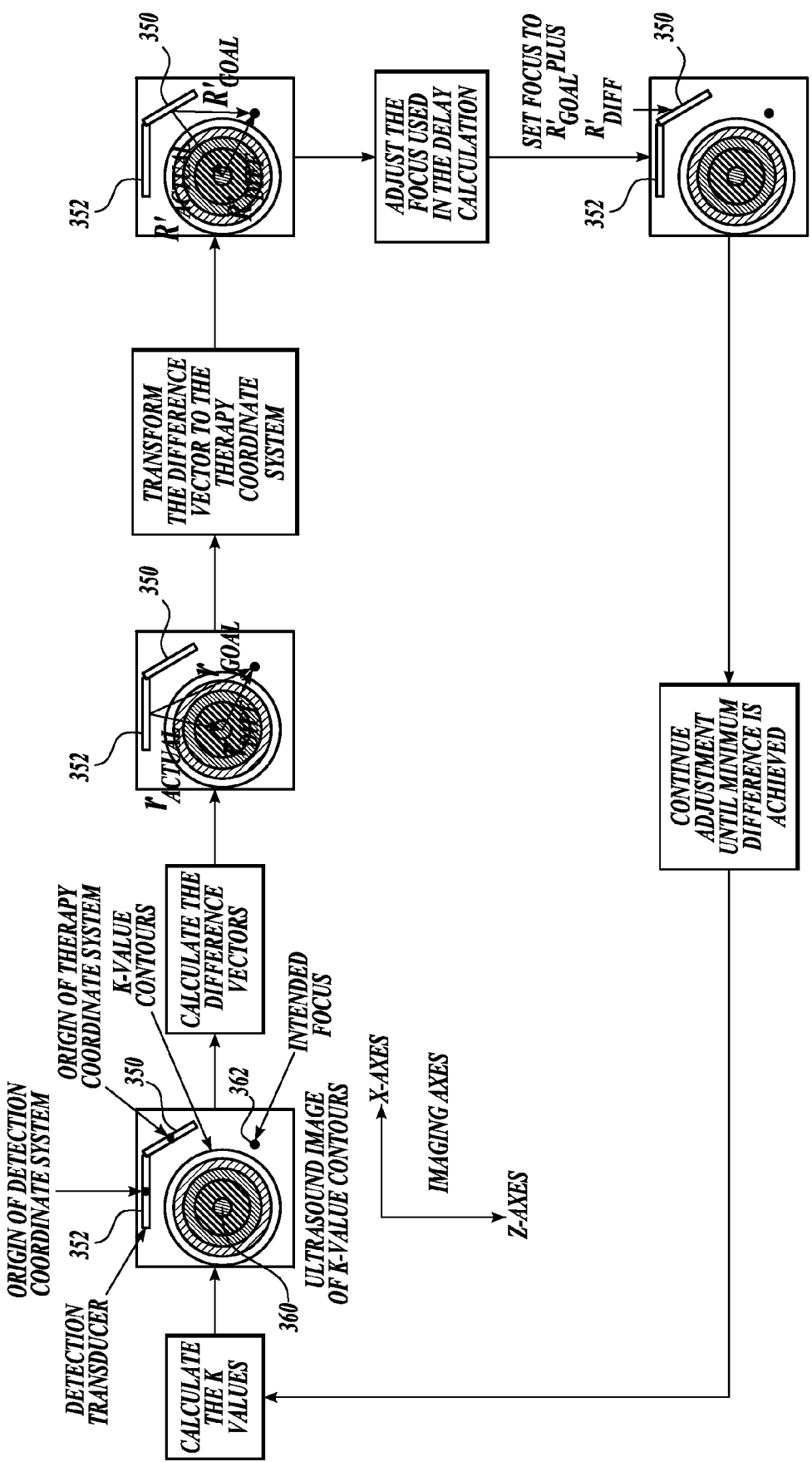
FIG. 15 illustrates a system for adjusting a focus point of a delivered HIFU signal in accordance with another aspect of the disclosed technology.

In addition or as an alternative to adjusting the energy of the delivered HIFU signals, the disclosed technology can be used to redirect the focus point of the delivered signals. In the embodiment shown in FIG. 15, a therapy transducer 350 delivers HIFU signals to a tissue sample. A detection transducer 352 receives the corresponding echo signals and computes K values at a number of positions in the tissue. In the example shown, the K values have a maximum value at a point 360 which is offset from an intended focus point 362 of the HIFU signals. By comparing the location of the maximum K value to the intended focus point, the system can determine if the focus point is misaligned. By computing the offset between the location of the maximum K value at 360 and the intended focus point at 362, a difference vector can be determined and the difference vector supplied to a beam forming equation used by a waveform generator to cause the therapy transducer 350 to redirect the focus point of the HIFU process towards the desired focus point 362. Alternatively, the difference vector can be supplied to a mechanical mechanism (not shown) that physically reorients the focus of the HIFU transducer. The process can continue by continuing to measure K values from the received echo signals and computing the location of the maximum K value and comparing it to the desired focus point until such time as the maximum K value is within a predetermined distance of the desired focus point.

Although illustrative embodiments of the disclosed technology have been illustrated and described, it will be appreciated that various changes can be made therein without departing from the spirit and scope of the technology. For example, the disclosed technology is not limited to medical applications but can be used in any environment such as industrial settings where there is a need to control the energy of a HIFU signal delivered. Therefore, the scope of the technology is to be determined solely by the following claims and equivalents thereof. In addition, the disclosed technology is not limited to the delivery of HIFU signals to the patient but can be applied to the delivery of any waveform such as non-focused ultrasound or laser light energy to a non-linear medium such as tissue.

The embodiments of the invention in which an exclusive property or privilege is claimed are defined as follows:

1. A method of adjusting an energy of a high intensity focused ultrasound (HIFU) signal delivered by a HIFU transducer, comprising:
   transmitting a HIFU signal having a fundamental frequency to a target volume;
   receiving ultrasound echo signals from one or more positions;
   determining an energy of the echo signals in a first frequency range and an energy of the echo signals in a second frequency range;
   comparing the energy of the echo signals in the first frequency range and the energy of the echo signals in the second frequency range by determining a ratio of a power of the echo signals in the first frequency range to a power of the echo signals in the second frequency range; and
   based on the comparison, adjusting one or more characteristics of the HIFU signal to adjust the energy of the HIFU signal delivered by the HIFU transducer.

2. The method of claim 1, wherein the first frequency range does not include the fundamental frequency of the HIFU signal and the second frequency range does include the fundamental frequency of the HIFU signal.

3. The method of claim 2, wherein the first frequency range includes one or more harmonics and/or sub-harmonics of the fundamental frequency of the HIFU signal.

4. The method of claim 3, wherein the first frequency range includes one or more odd harmonics of the fundamental frequency of the HIFU signal.

5. The method of claim 1, wherein the energy of the HIFU signal delivered by the HIFU transducer is adjusted by:
   determining if the ratio at a selected position is less than a threshold, and if so, adjusting a characteristic of the HIFU signal to increase the delivered energy of the HIFU signal at the selected position.

6. The method of claim 1, wherein the energy of the HIFU signal delivered by the HIFU transducer is adjusted by:
   determining if the ratio at a selected position is greater than a threshold, and if so, adjusting a characteristic of the HIFU signal to decrease the delivered energy of the HIFU signal at the selected position.

7. The method of claim 1, wherein the energy of the echo signals in the first frequency range and the energy of the echo signals in the second frequency range are further compared by:

determining a difference in phase between the echo signals in the first frequency range and the echo signals in the second frequency range.

8. The method of claim 7, wherein the one or more characteristics of the HIFU signal is adjusted based on a magnitude of the difference in phase.

9. A system for applying HIFU signals to a subject, comprising:

a HIFU controller configured to produce electronic HIFU driving signals having one or more adjustable characteristics that affect the energy of a delivered HIFU signal;

a HIFU transducer configured to receive the electronic HIFU driving signals, produce acoustic HIFU signals with a fundamental frequency, and deliver the acoustic HIFU signals to the subject;

a receiving transducer configured to detect echo signals from the subject; and an ultrasound processor configured to receive the detected echo signals and compare the energy of the echo signals in a first frequency range to the energy of the echo signals in a second frequency range to produce a feedback signal that is used to adjust one or more of the characteristics of the HIFU driving signals to adjust the energy of the HIFU signal delivered, wherein the ultrasound processor is configured to compute a ratio of a power of the echo signals in the first frequency range and a power of the echo signals in the second frequency range and compare the ratio to stored data that correlates the ratio to delivered energy of a HIFU signal to produce the feedback signal.

10. The system of claim 9, wherein the feedback signal is perceptible by a physician to manually adjust one or more of the characteristics of the electronic HIFU driving signals.

11. The system of claim 9, wherein the feedback signal is an electronic signal supplied to the HIFU controller to electronically adjust one or more of the characteristics of the electronic HIFU driving signals.

12. The system of claim 9, wherein the first frequency range includes one or more harmonics of the fundamental frequency of the HIFU signals and the second frequency range includes the fundamental frequency of the HIFU signals.

13. The system of claim 9, wherein the receiving transducer is the HIFU transducer.

14. The system of claim 9, wherein the receiving transducer is an ultrasound imaging transducer.

15. The system of claim 9, wherein the receiving transducer is a polyvinylidene fluoride (PVDF) transducer.

16. The system of claim 9, wherein the receiving transducer is a hydrophone.

17. The system of claim 9, wherein the ultrasound processor further compares a phase difference between the echo signals in the first frequency range and the echo signals in the second frequency range to produce the feedback signal.

18. A system for applying HIFU signals to a subject, comprising:

a HIFU controller configured to produce electronic HIFU driving signals having one or more adjustable characteristics that affect the energy of a delivered HIFU signal;

a HIFU transducer configured to receive the electronic HIFU driving signals, produce acoustic HIFU signals with a fundamental frequency, and deliver the acoustic HIFU signals to tissue of the subject;

a receiving transducer configured to detect echo signals from the tissue of the subject;

a processor configured to receive the echo signals and compare the energy of the echo signals in a first frequency range to the energy of the echo signals in a second frequency range at a number of locations in the tissue by computing a ratio of the power of the echo signals in the first frequency range to the power of the echo signals in the second frequency range; and a display on which an image of the tissue is displayed along with an image representative of the comparison at one or more locations in the tissue.

19. The system of claim 18, wherein the processor is further configured to quantify the ratio in a visually perceptible form.

20. The system of claim 19, wherein the visually perceptible form is a color code.

* * * * *